(12) United States Patent
McClymont et al.

(10) Patent No.: US 12,661,099 B2
(45) Date of Patent: Jun. 23, 2026

(54) ARM ATTACHMENT FOR RETRACTOR AND RETRACTOR BLADES

(71) Applicant: VB Spine US Opco LLC, Leesburg, VA (US)

(72) Inventors: Kaitlin Elizabeth Anne McClymont, Reston, VA (US); Nicholas Padovani, Fairfax, VA (US); Pauline Patricia Hutton, Gainesville, VA (US); Robert J. Tokash, Stephens City, VA (US)

(73) Assignee: VB Spine US Opco LLC, Leesburg, VA (US)

( * ) Notice: Subject to any disclaimer, the term of this patent is extended or adjusted under 35 U.S.C. 154(b) by 523 days.

(21) Appl. No.: 18/137,211

(22) Filed: Apr. 20, 2023

(65) Prior Publication Data

US 2024/0350129 A1 Oct. 24, 2024

(51) Int. Cl.
| | |
|---|---|
| *A61B 17/02* | (2006.01) |
| *A61B 17/28* | (2006.01) |
| *A61B 17/00* | (2006.01) |

(52) U.S. Cl.
CPC ...... *A61B 17/0206* (2013.01); *A61B 17/2833* (2013.01); *A61B 2017/00464* (2013.01)

(58) Field of Classification Search
CPC . A61B 17/02; A61B 17/0206; A61B 17/0218; A61B 17/2833; A61B 90/50
See application file for complete search history.

(56) References Cited

U.S. PATENT DOCUMENTS

| | | | |
|---|---|---|---|
| 5,984,865 A | 11/1999 | Farley et al. | |
| 6,042,540 A | 3/2000 | Johnston et al. | |
| 6,733,444 B2 | 5/2004 | Phillips | |
| 6,736,775 B2 | 5/2004 | Phillips | |
| 6,860,850 B2 | 3/2005 | Phillips et al. | |
| 6,887,197 B2 | 5/2005 | Phillips | |
| 6,887,198 B2 | 5/2005 | Phillips et al. | |
| 7,004,943 B2 | 2/2006 | Ferrante et al. | |
| 7,569,014 B2 | 8/2009 | Bass et al. | |

(Continued)

FOREIGN PATENT DOCUMENTS

| | | |
|---|---|---|
| WO | 2019055173 A1 | 3/2019 |
| WO | 2021118759 A1 | 6/2021 |

OTHER PUBLICATIONS

Extended European Search Report including Search Opinion from EP Appl. No. 24171089.6, dated Oct. 18, 2024, pp. 1-9.

*Primary Examiner* — Si Ming Ku

(74) *Attorney, Agent, or Firm* — Lerner David LLP

(57) ABSTRACT

An apparatus for holding a retractor arm including a connector attachable at a free end of a support arm. The connector including a housing extending with a receptacle, a holder block movably disposed in the housing, and a bumper block movably disposed in the housing. The holder block adjustable between a retracted position where a tip of the holder block is outside of the receptacle and a holding position where the tip is at least partially within the receptacle. The bumper block being biased in an expanded position such that the holder block is held in the retracted position by the bumper block and movement of the bumper block from the expanded position to a compressed position releases the holder block. The connector is adapted to receive a post disposed on a retractor arm, the post being loadable into the receptacle to cause the bumper block to move.

22 Claims, 17 Drawing Sheets

(56) References Cited

U.S. PATENT DOCUMENTS

| | | |
|---|---|---|
| 7,588,537 B2 | 9/2009 | Bass |
| 8,257,255 B2 | 9/2012 | Farley et al. |
| 8,357,087 B2 | 1/2013 | Fetzer |
| 8,360,971 B2 | 1/2013 | Farley et al. |
| 8,425,404 B2 | 4/2013 | Wilson et al. |
| 8,449,463 B2 | 5/2013 | Nunley et al. |
| 8,636,657 B2 | 1/2014 | Hamada |
| 8,900,137 B1 | 12/2014 | Lovell et al. |
| 8,974,381 B1 | 3/2015 | Lovell et al. |
| 9,078,635 B2 | 7/2015 | Menendez et al. |
| 9,237,933 B2 | 1/2016 | Agbodoe et al. |
| 9,320,506 B2 | 4/2016 | Bertagnoli et al. |
| 9,782,316 B2 | 10/2017 | Schuerch, Jr. et al. |
| 9,795,367 B1 | 10/2017 | Lee et al. |
| 9,848,862 B2 | 12/2017 | Bass et al. |
| 9,872,675 B2 | 1/2018 | Nowak et al. |
| 9,918,795 B2 | 3/2018 | Wyslucha et al. |
| 10,130,348 B2 | 11/2018 | Cryder et al. |
| 10,172,515 B2 | 1/2019 | Coleman et al. |
| 10,792,049 B2 | 10/2020 | Fiedler et al. |
| 10,874,571 B2 | 12/2020 | Zahynacz |
| 10,893,855 B2 | 1/2021 | Truckey |
| 2007/0055110 A1 | 3/2007 | Bass |
| 2012/0271119 A1 | 10/2012 | White |
| 2017/0231613 A1 | 8/2017 | Casey et al. |
| 2017/0296160 A1 | 10/2017 | O'Brien |
| 2018/0271509 A1 | 9/2018 | Truckey |
| 2019/0209154 A1 | 7/2019 | Richter et al. |
| 2020/0214686 A1 | 7/2020 | Truckey et al. |
| 2020/0281576 A1 | 9/2020 | Garcia et al. |
| 2020/0352676 A1 | 11/2020 | Schlosser et al. |
| 2020/0367875 A1 | 11/2020 | Nowak et al. |
| 2021/0068801 A1 | 3/2021 | Capote et al. |
| 2021/0153857 A1 | 5/2021 | Hill et al. |
| 2021/0169462 A1 | 6/2021 | Nowak |
| 2021/0196256 A1 | 7/2021 | Casey et al. |
| 2023/0013570 A1* | 1/2023 | White ............... A61B 17/0206 |

* cited by examiner

1100

100A

200A

710

100B

200B

1100

700

200A

100A

710

200B

100B

ARM ATTACHMENT FOR RETRACTOR AND RETRACTOR BLADES

BACKGROUND

In the field of spine surgery, there is an ongoing concern involving the adequacy of retractors and arms used to support such retractors that are employed to access surgical sites. Among other considerations, adequacy may be determined based on the ease and speed of deployment and the degree to which a position of a retractor is commensurate with a desired degree of movement in space.

Various surgical techniques employ retraction tools specifically designed to improve accessibility to a surgical site. Such tools may often be difficult to position and often require additional time and assistance to setup and adjust during a surgical operation. For example, it may be difficult to position and mount hand-held blades during the creation of an access portal for surgery on the spine. In some cases, an antero-lateral surgery may involve positioning and using a hand-held blade, followed by securement of a position of such hand-held blade with a support arm, where the hand-held blade and the support arm are connected while holding each of the hand-held blade and the support arm with respective free hands, and, through a third free hand, securing a locking feature to affix the position of the hand-held blade relative to the support arm. Depending on the positioning of the hand-held blade, connecting it with a support arm may be further complicated by a difficult connection angle. Further, because in many procedures more than one blade is secured to a support arm, such difficulties that arise from securing a blade to an arm are compounded. Additionally, intraoperative adjustments of the hand-held blades during a surgical procedure present similar difficulties which may render the surgical procedure more cumbersome and increase the likelihood of problems arising as a result. Accordingly, while retraction tools are necessary to provide adequate access to surgical sites, their use is often cumbersome, involves extensive labor to ensure all tools are adequately secured, and requires experienced surgical personnel.

Thus, there is a need for improved retraction tools and accessories that allow for the efficient creation of a secure access to a surgical site.

BRIEF SUMMARY

Some aspects herein relate to a system that may include a support arm with a connector at one end and a retraction tool, such as a hand-held retractor blade. The connector is configured to be connectable with an attachment structure on the hand-held blade. The support arm may also be connected to other retraction tools, such as a retractor frame that holds retractor blades. A method of utilizing the connector allows for the free end of the support arm to be connected to the retraction tool from a variety of angles. Once connected, the connector may provide a provisional connection that allows the retraction tool to rotate freely with respect to the fixed end of the support arm thereby permitting the retraction tool to be positioned and adjusted after being connected to the support arm. By providing this provisional connection, the connector eliminates the need to hold each of the support arm and the retraction tool while fixing them to each other, thereby freeing up a hand, or in other words, reducing the number of hands needed. With a hand freed up, the provisional connection reduces the difficulty of arranging and attaching the support arm to the retraction tool while keeping the retraction tool supported by the support arm. This provisional connection also reduces the complexity of arranging and rearranging retraction tools during a surgical operation.

After the retraction tool and the support arm have been positioned, an actuation mechanism on the attachment structure of the retraction tool, such as a knob threadably received on a post, may be actuated to fix the connector to the retraction tool. This fixation is reversable and accordingly the actuation may be performed in reverse to return the position from fixed attachment to a provisional attachment, as described above. In this manner, the attachment structure may be loosened without worry of the support arm becoming completely disconnected from the retraction tool.

Another aspect of the present disclosure relates to an embodiment of a connector device that may be used to connect various surgical arms with retractor instruments, such as hand-held blades. The components of the connector device may include a trigger, a spring-loaded plug, a casing with an insertion channel adjacent to a first end, and a threaded extension at a second end opposite the first end. The casing is configured with slots to hold the trigger and the spring-loaded plug. The connector device operates such that when the trigger is pressed further into a cavity within the casing, the displacement of the trigger releases the spring-loaded plug such that a leading end of the plug advances into a region of the insertion channel. The trigger may be disposed on a periphery of the insertion channel. If released as a result of the placement of an object into the insertion channel, the spring-loaded plug ejects from a slot within the connector device to hold the object within the insertion channel. Such attachment is provisional in that the object may still be rotated and moved slightly within the insertion channel, while simultaneously being held in place within the insertion channel. The insertion channel is configured to receive various elongated objects (e.g., a rod) that function as a fastener component for a retractor tool. The connector device may provide an interim or fixed connection between various medical tools such as blades, retractor frames, and support structure together and allows for easy repositioning and adjustments of such tools during surgical operations without fully disconnecting the tools. The connector device connects medical tools by engaging with a fastener component disposed on the medical tool. To fully disconnect medical tools from the connector, the spring-loaded plug is retracted into a slot of the connector device by pulling on a knob in a direction away from the insertion channel.

In a first aspect, the present disclosure relates to an apparatus for holding a retractor. In a first embodiment of the first aspect, an apparatus for holding a retraction device includes a connector attachable to a free end of a support arm. The retraction device may be a hand-held blade or a retractor frame, for example. The connector includes a housing extending from a proximal end to a distal end, a holder block movably disposed in the housing, and a bumper block movably disposed in the housing. The housing including a receptacle adjacent to the distal end. The holder block adjustable between a retracted position where a tip of the holder block is outside of the receptacle and a holding position where the tip is at least partially within the receptacle. The bumper block including a surface defining part of the receptacle. The bumper block being biased in an expanded position such that the holder block is held in the retracted position by the bumper block and movement of the bumper block from the expanded position to a compressed position releases the holder block into holding position. The connector is adapted to receive a post disposed on a retraction device, the post being loadable into the receptacle to cause the bumper block to move from the expanded position to the compressed position such that the holder block snaps onto and holds the post within the receptacle while the post remains rotatable relative to the connector. In some examples, the post may be side-loadable into the receptacle.

In a second example of the first embodiment, the holder block of the connector may be manually adjustable from the blocked position to the unblocked position. In a third example of the first embodiment, the holder block of the connector may be pivotally movable or slidably movable. In a fourth example of the first embodiment, the bumper block of the connector may be supported by a spring connecting the bumper block to the housing. In a fifth example of the first embodiment, the connector includes a loading axis passing through the center of the receptacle, the center of the side-facing periphery of the receptacle, and the bumper block, the holding block being entirely offset from the loading axis when the holder block is in the retracted position.

In a sixth example of the first embodiment, a system including the apparatus mentioned above and a hand-held blade with a post disposed thereon. The post being loadable into the receptacle of the connector, and the post including a rotatable head adapted to fix the hand-held blade to the connector. In a seventh example of the first embodiment, the system may include a connector including a first set of teeth and a hand-held blade including a second set of teeth. The first and the second set of teeth engageable with each other when the head of the post is rotated, thereby fixing the hand-held blade to the connector.

In a second aspect, the present disclosure relates to a system for engagement of a retraction device to a support arm. In a first embodiment of the second aspect, a system for engagement of a retraction device to a support arm includes a connector attached at an end of a support arm. The connector includes a housing extending from a proximal end to a distal end, a holder block movably disposed in the housing, and a retraction device engageable with the connector. The housing including a receptacle adjacent to the distal end. The holder block adjustable between a retracted position where a tip of the holder block is outside of the receptacle and a holding position where the tip is at least partially within the receptacle. The retraction device including a post disposed thereon. The post comprises a head and a shaft extending from the head, the shaft adapted to be received in the receptacle. When the shaft is loaded into the receptacle of the housing, the connector limits movement of the retraction device in a longitudinal axis of the shaft. When the shaft is loaded into the receptacle of the housing and the head of the post may be rotated so that a first set of teeth on a bottom surface of the housing engage a second set of teeth on the retraction device, the connector is rotatably fixed relative to the retraction device.

In a second embodiment of the second aspect, the post further comprises a threaded base disposed in an opening of the retraction device, the threaded base having a bore defined by an inner threaded surface that a threaded surface of the shaft is rotatably disposed in the bore. In a third embodiment of the second aspect, the threaded base includes the second set of teeth being disposed thereon. In a fourth embodiment of the second aspect, when the post is advanced into and received in the receptacle, the holder block passively moves form the retracted position to the holding position. In a fifth embodiment of the second aspect, the connector includes a third set of teeth on a top surface of the housing opposite the first set of teeth and the head of the post includes a fourth set of teeth adapted to engage the third set of teeth when the head is rotated to fix the connector to the post. In a sixth embodiment of the second aspect, the retraction device may be a hand-held blade or a portion of a retractor frame. In a seventh embodiment of the second aspect, the connector further comprises a bumper block disposed in the housing, the bumper block being adjustable from an expanded position to a compressed position, and the bumper block being adapted to hold the holder block in the retracted position when the bumper block is in the expanded position and to release the holder block when moved into the compressed position. In an eighth embodiment of the second aspect, the holder block may be pivotally movable or slidably movable.

In accordance with a third aspect, the present disclosure relates to a method for securing a retraction device to a support arm. In a first embodiment of the third aspect, the connector may be used in a procedure to secure a retractor frame or a hand-held blade to a support arm. In the procedure, the retractor frame or the hand-held blade are brought to the connector on a support arm with the holder block of the connector being in the retracted position (i.e., open position); the post of the retractor frame or hand-held blade is loaded into the receptacle on the connector and the holder block is moved into part of the receptacle once the post is within the receptacle such that the post is held in the connector while being freely rotatable in the connector; and the head of the post is rotated in a first direction until the first gripping surface of the connector engages a second gripping surface of the post, thereby fixing the post to the connector. In a second embodiment of the third aspect, the procedure may include, when the head is rotated, the head engaged with a first set of teeth on the connector with a second set of teeth on the retractor frame or the hand-held blade. In a third embodiment of the third aspect, the procedure may include, when the head is rotated, the head engaged with a third set of teeth on the connector with a fourth set of teeth on the retractor frame or the hand-held blade. In a fourth embodiment of the third aspect, the procedure may further include, the bumper block defining part of the receptacle of the connector being compressed when loading the post into the receptacle such that the compression of the bumper block causes the holder block to be released from an initial retracted position partially enveloping the post within the receptacle. In a fifth embodiment of the third aspect, the procedure may further include the post being removed from the receptacle, the removal process includes the head of the post being rotated in a second direction, the holder block being pulled on and held so as to move the holder block from the holding position (i.e., closed position) to the retracted position (i.e., open position), and the post being withdrawn from the receptacle of the connector. In a sixth embodiment of the third aspect, the procedure may include the holder block snapped into the retracted position when moved behind the bumper block while the holder block is being pulled.

BRIEF DESCRIPTION OF THE DRAWINGS

A more complete appreciation of the subject matter of the present disclosure and the various advantages thereof may be realized by reference to the following detailed description which refers to the accompanying drawings, in which.

5                                                                 6

Figure 2:
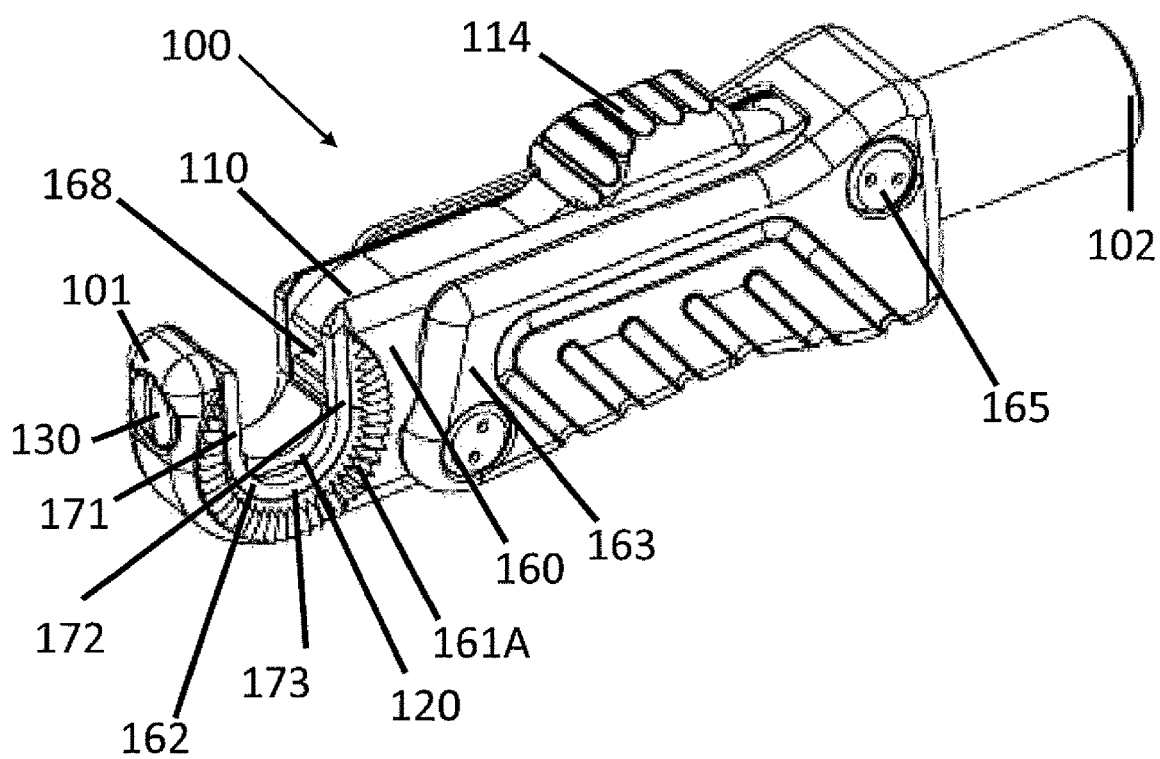
FIG. 2 is a perspective view of a connector in accordance with one embodiment of the present disclosure.
Figure 3:
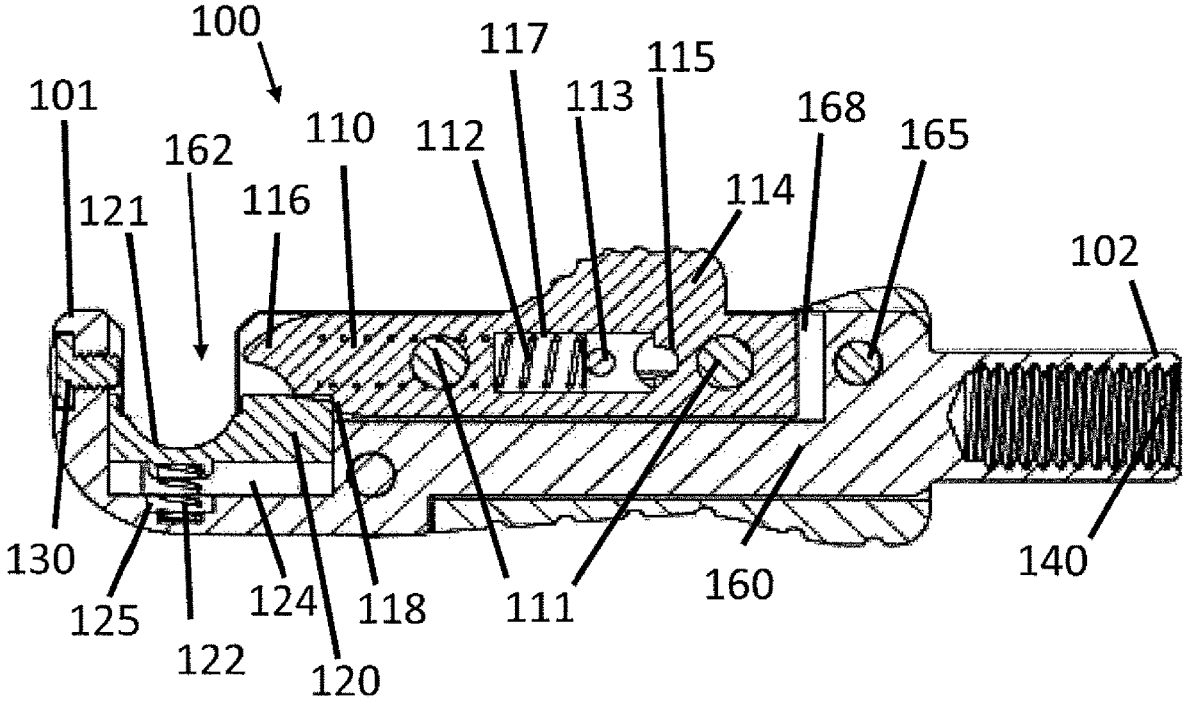
Figure 4:
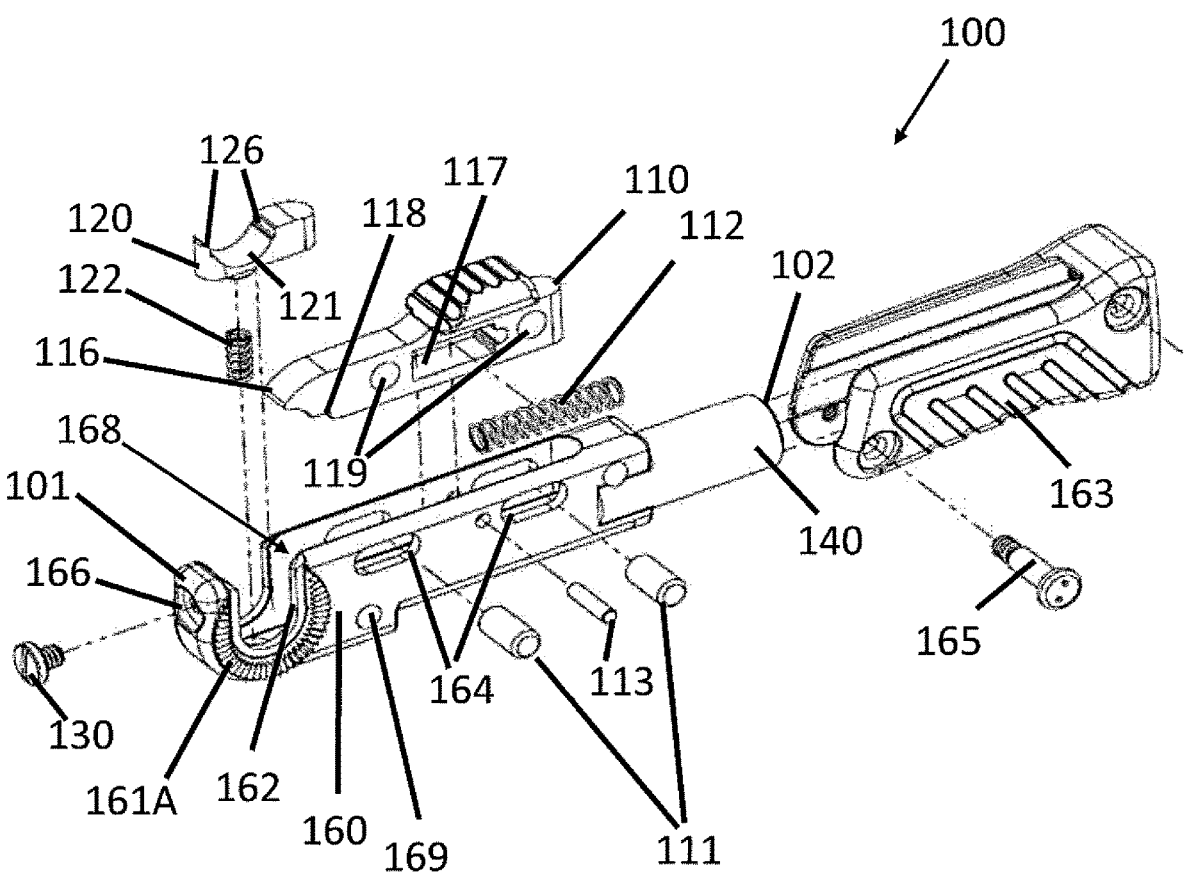
Figure 5:
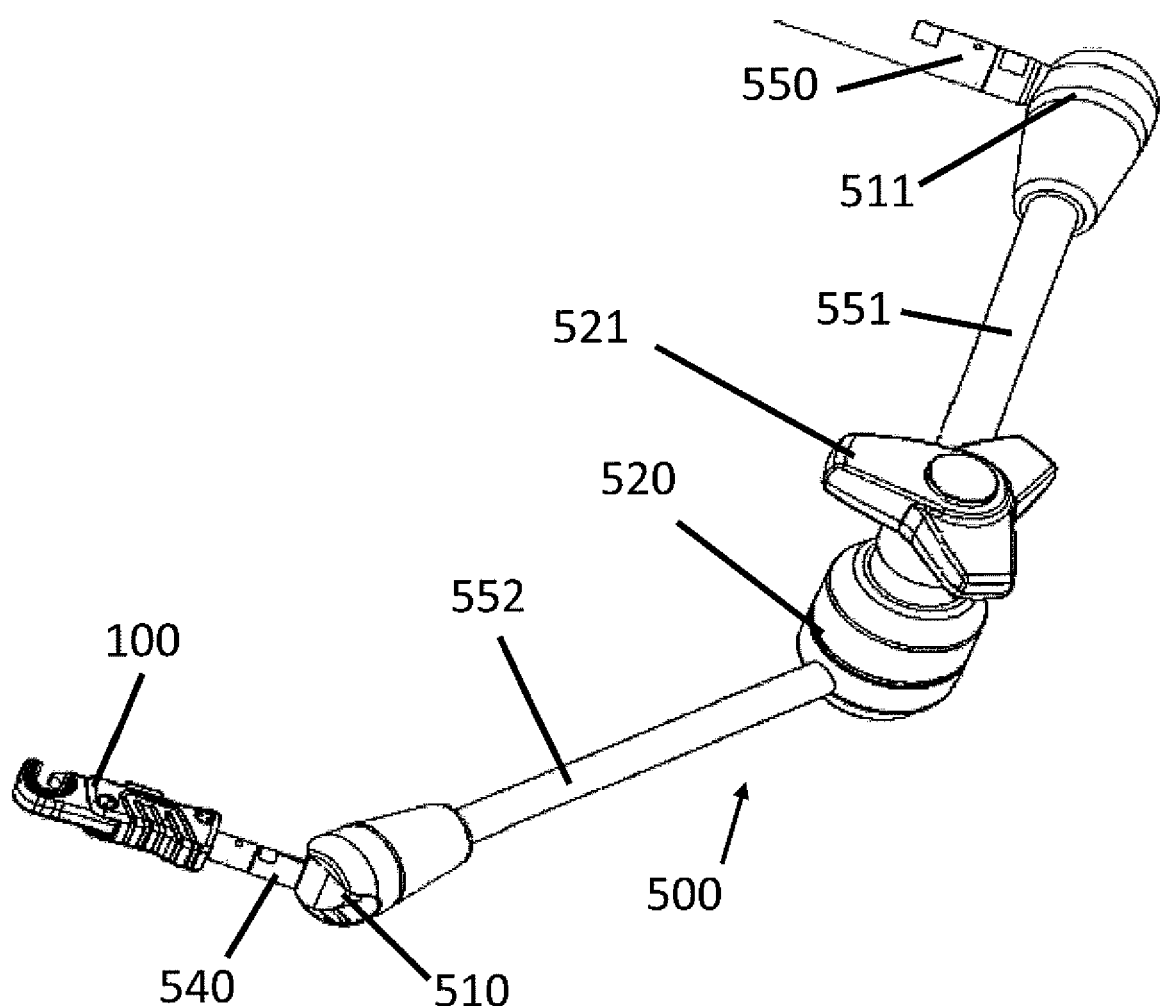
Figure 6:
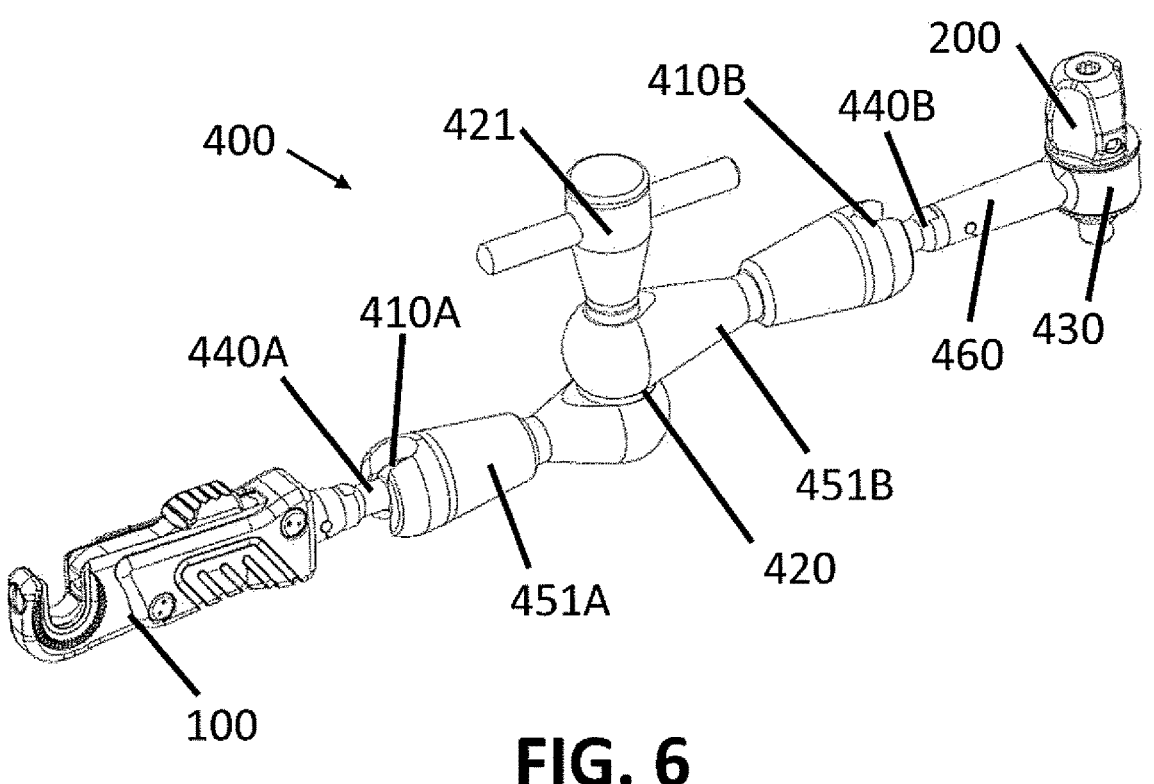
Figure 7:
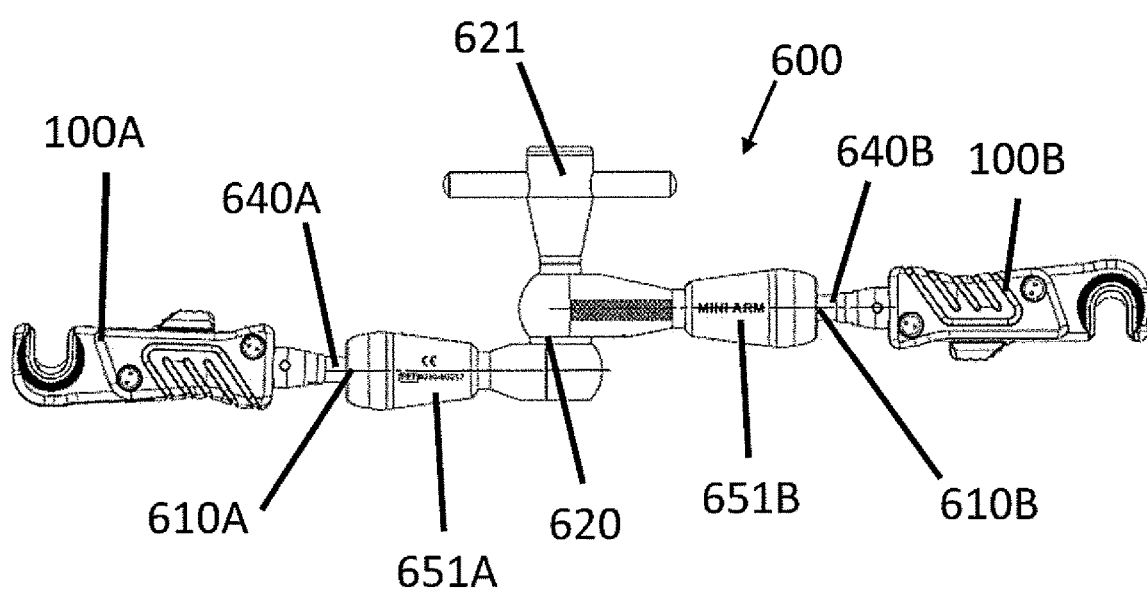
Figure 8:
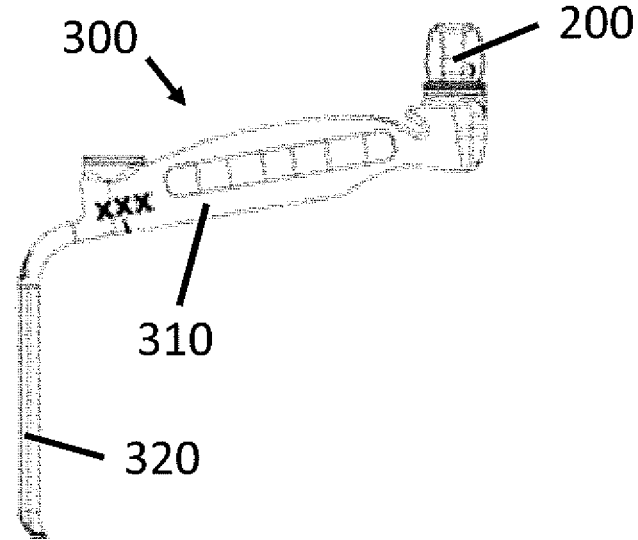
Figure 9:
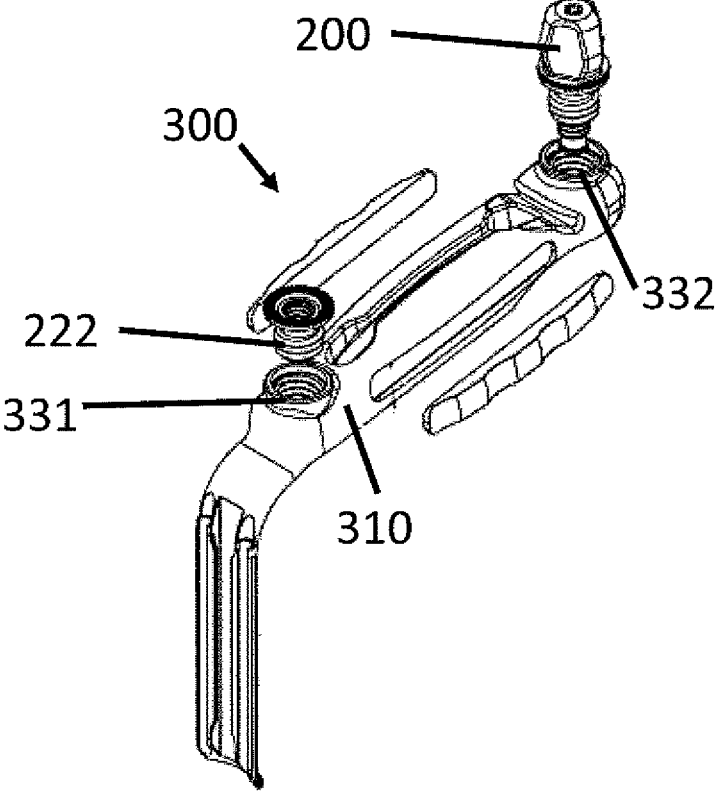
Figure 10A:
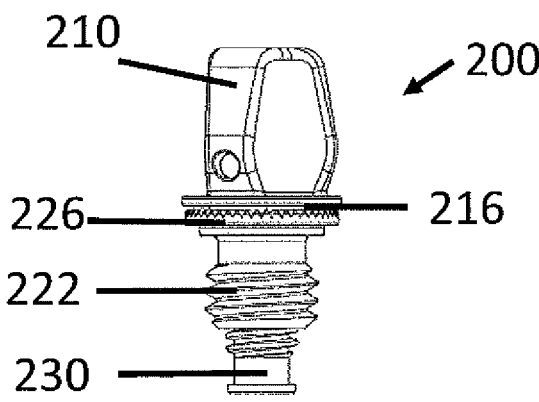
Figure 10B:
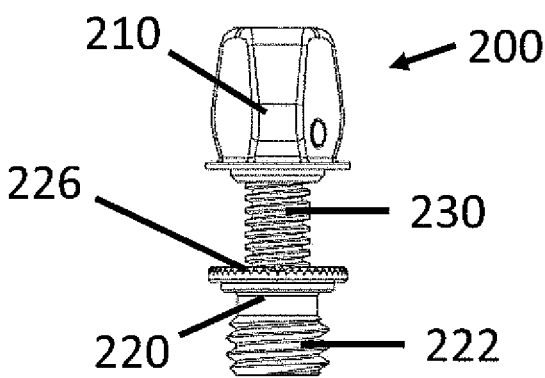
Figure 10C:
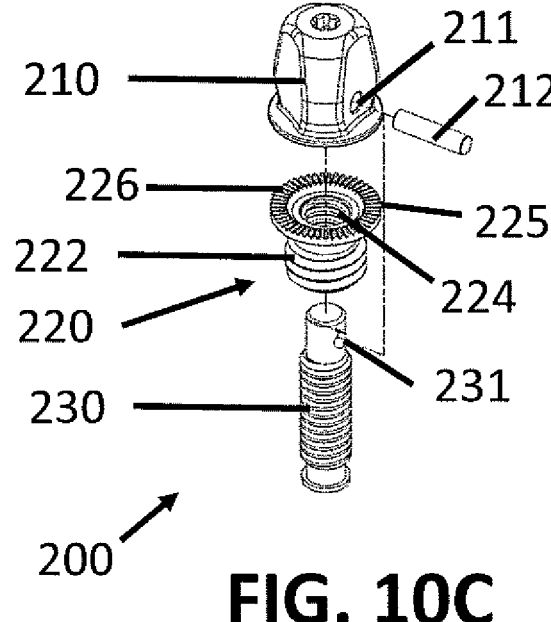
Figure 11:
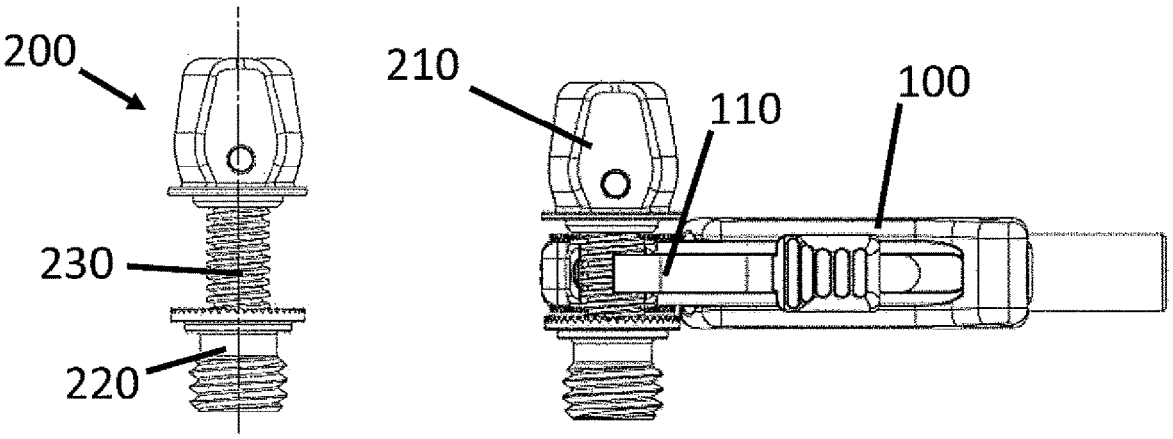
Figure 12:
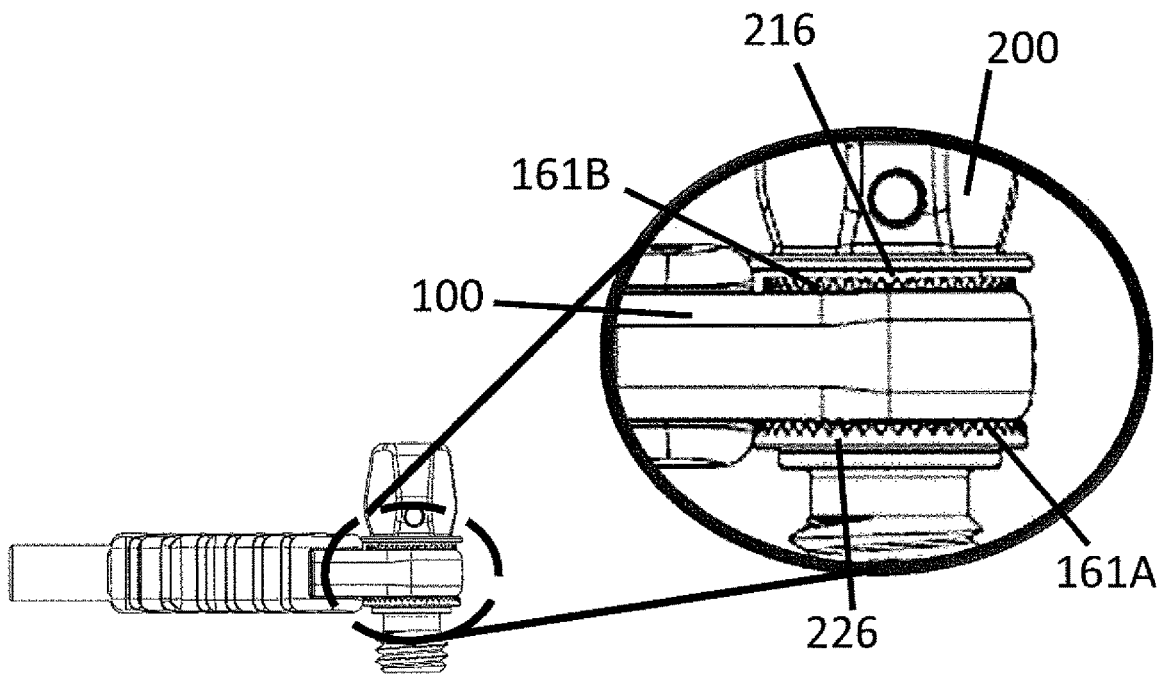
Figure 13:
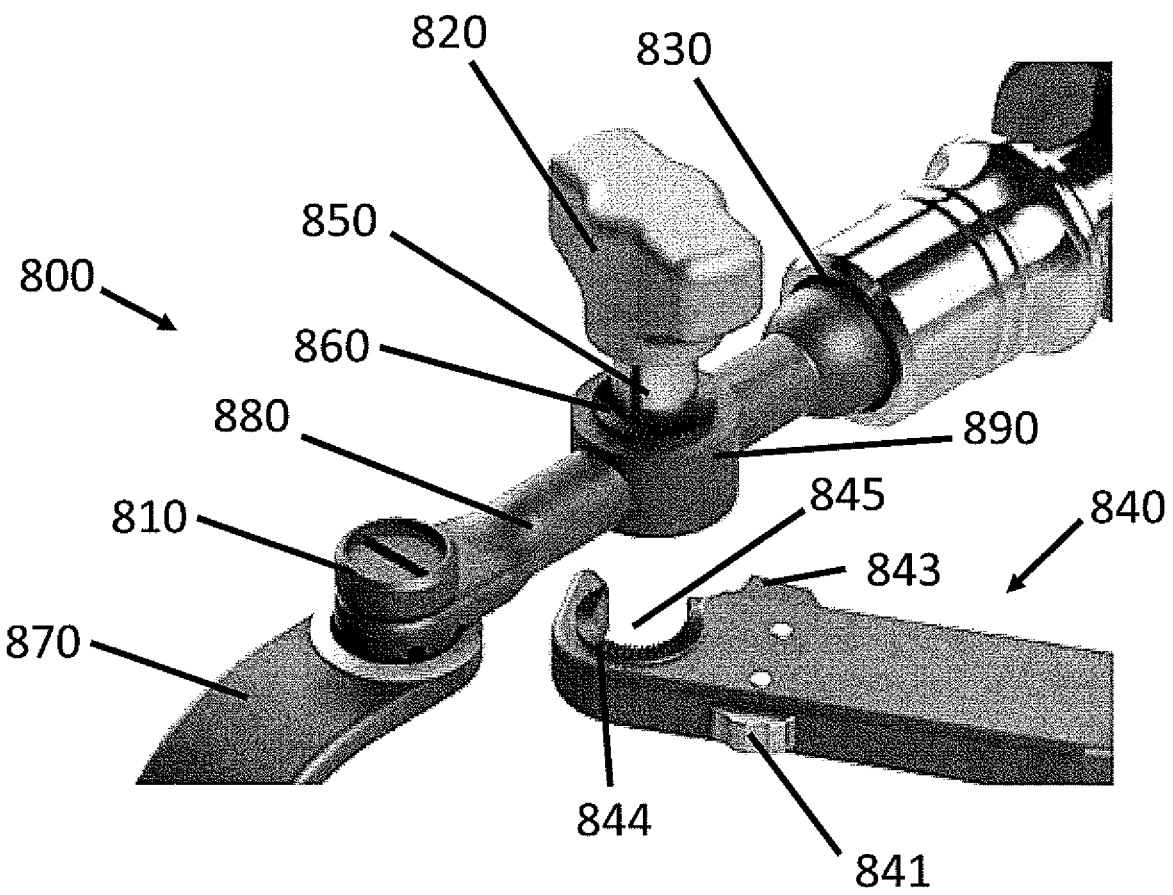
Figure 14:
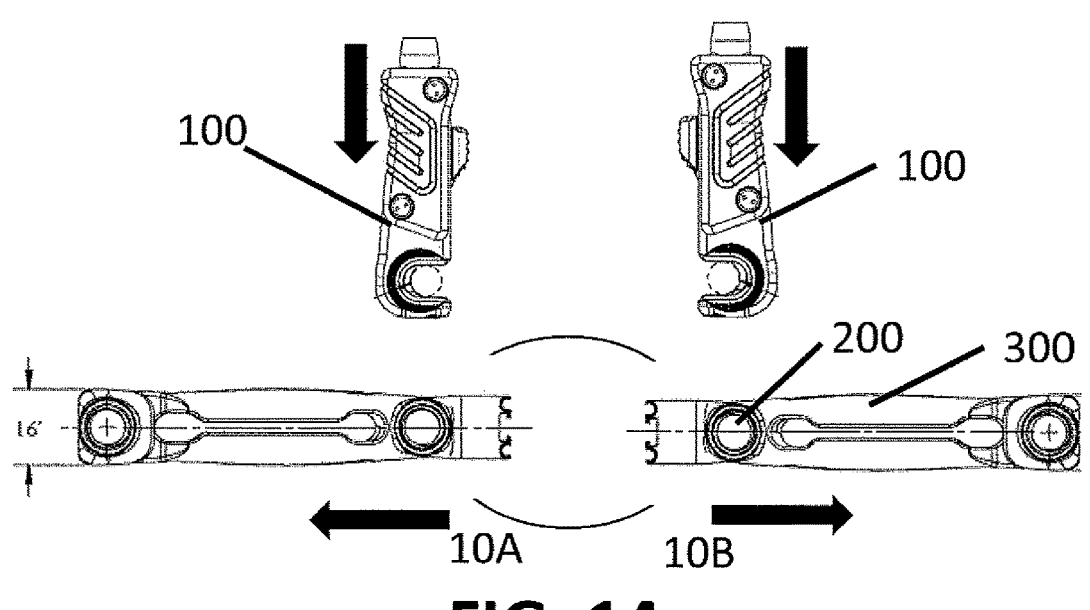
Figure 15:
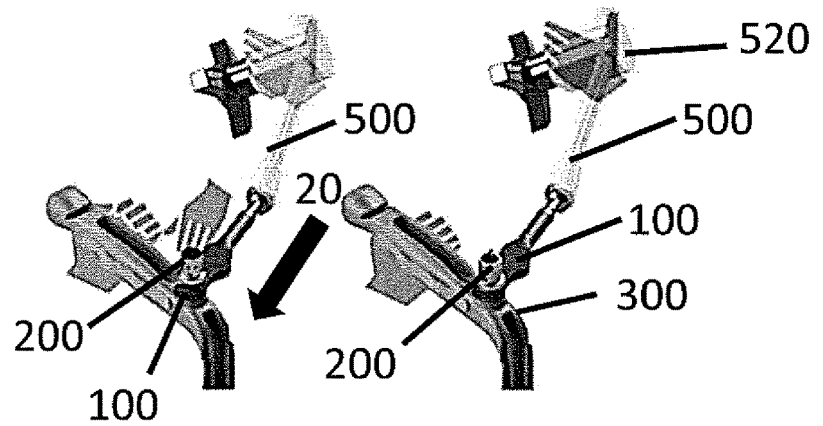
Figure 16:
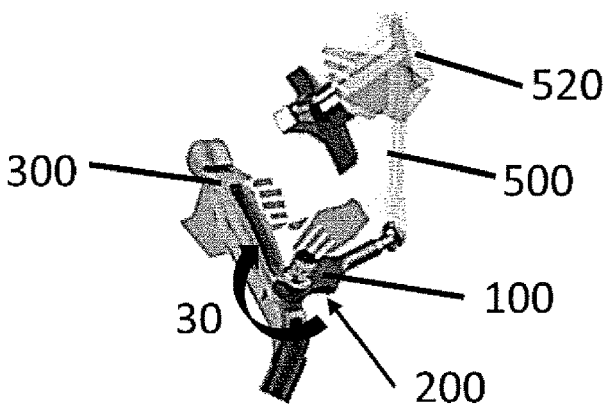
Figure 17A:
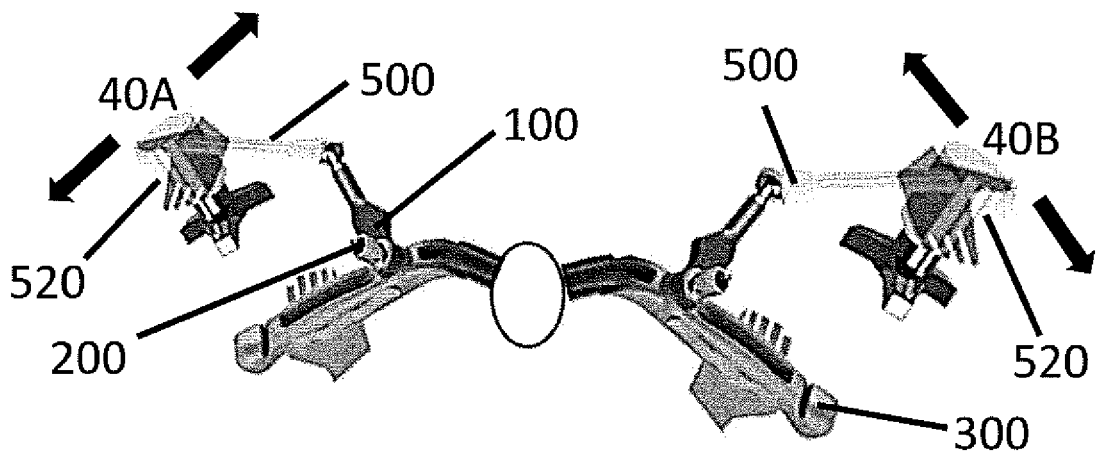
Figure 17B:
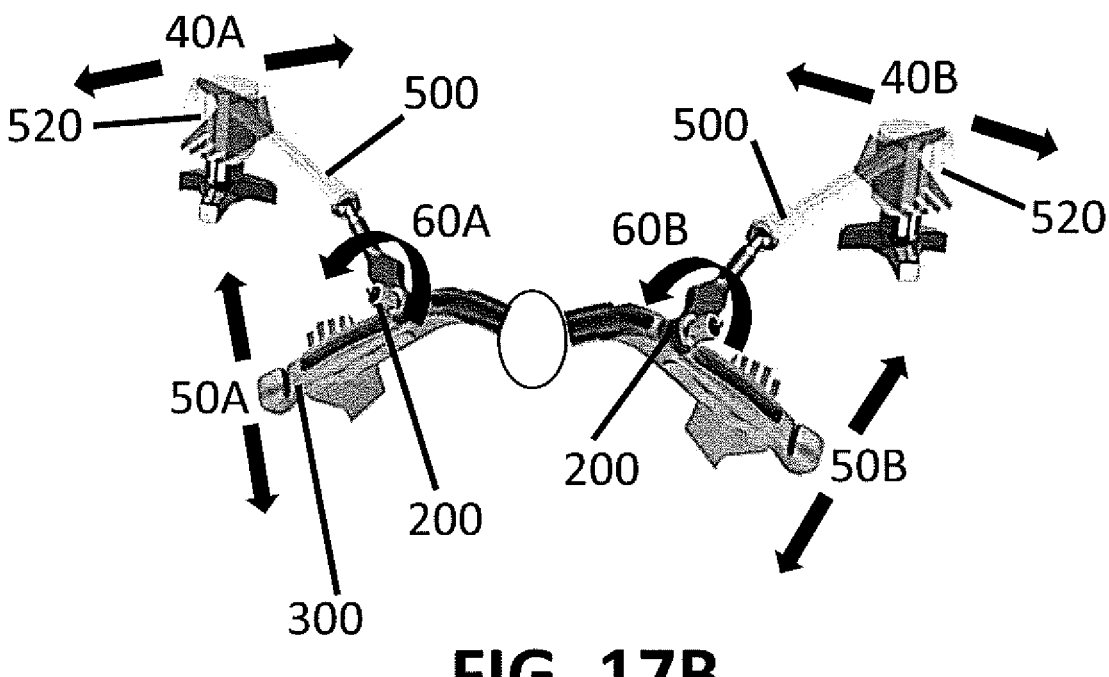
Figure 18:
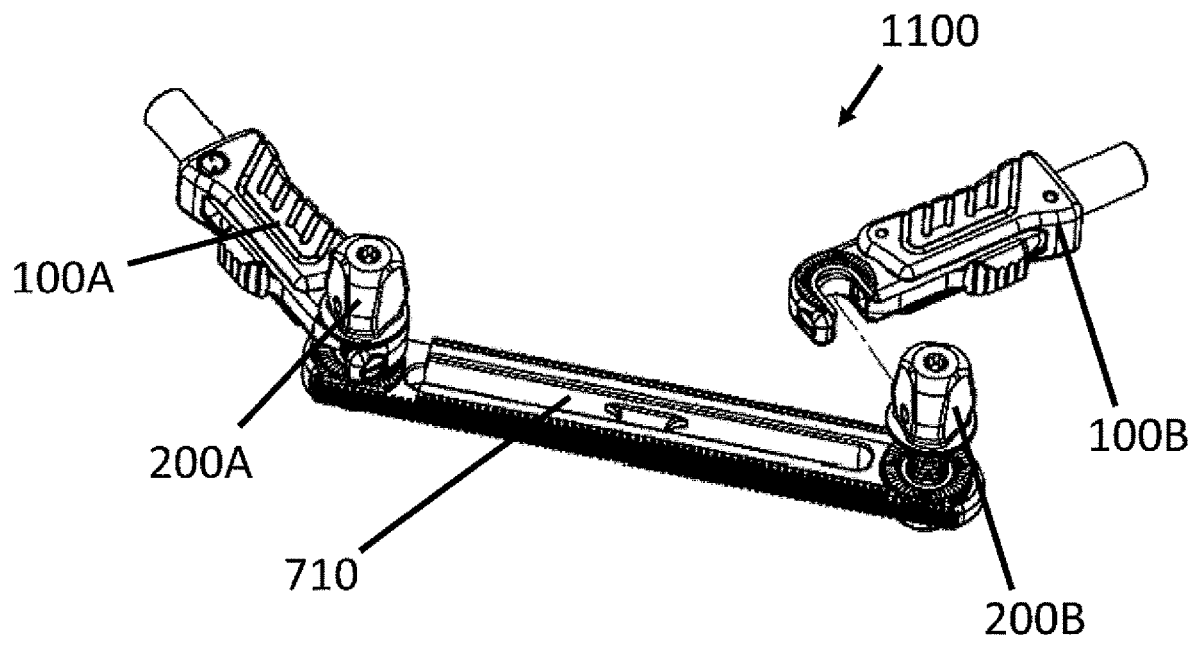
Figure 19:
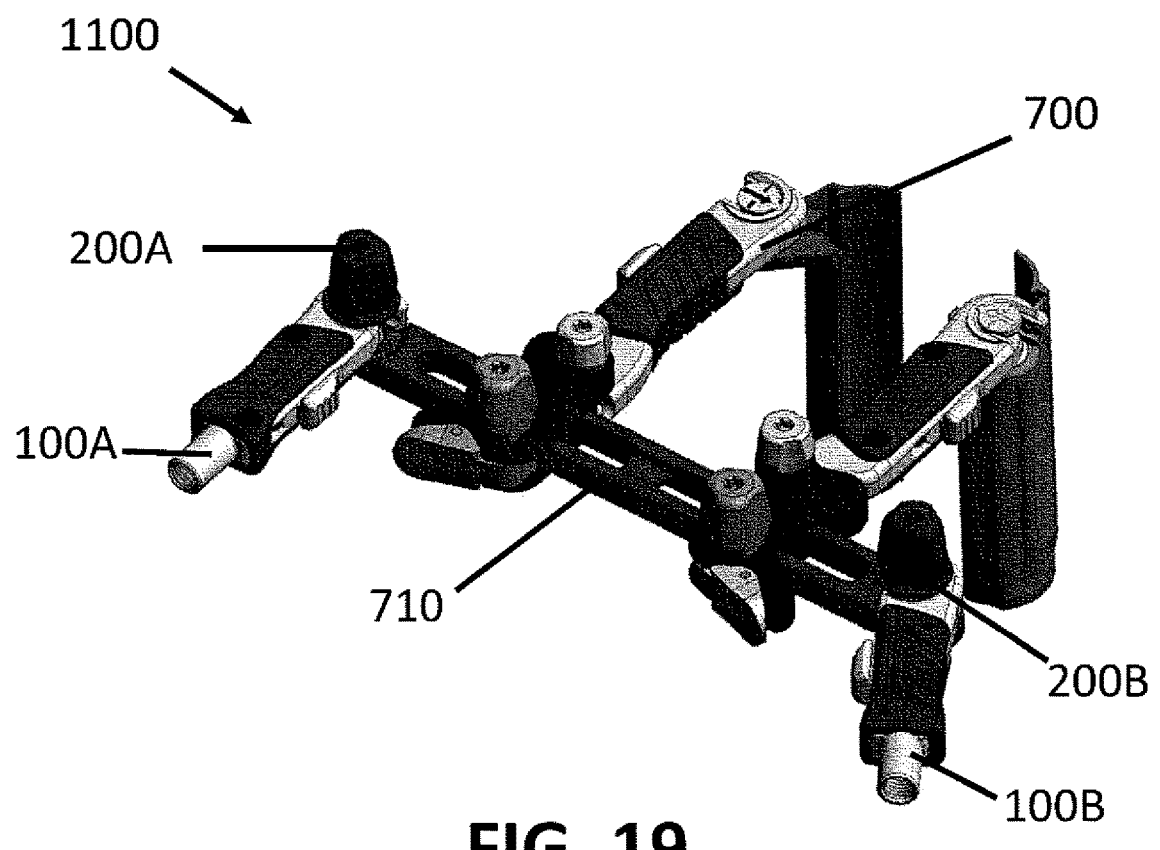
Figure 20:
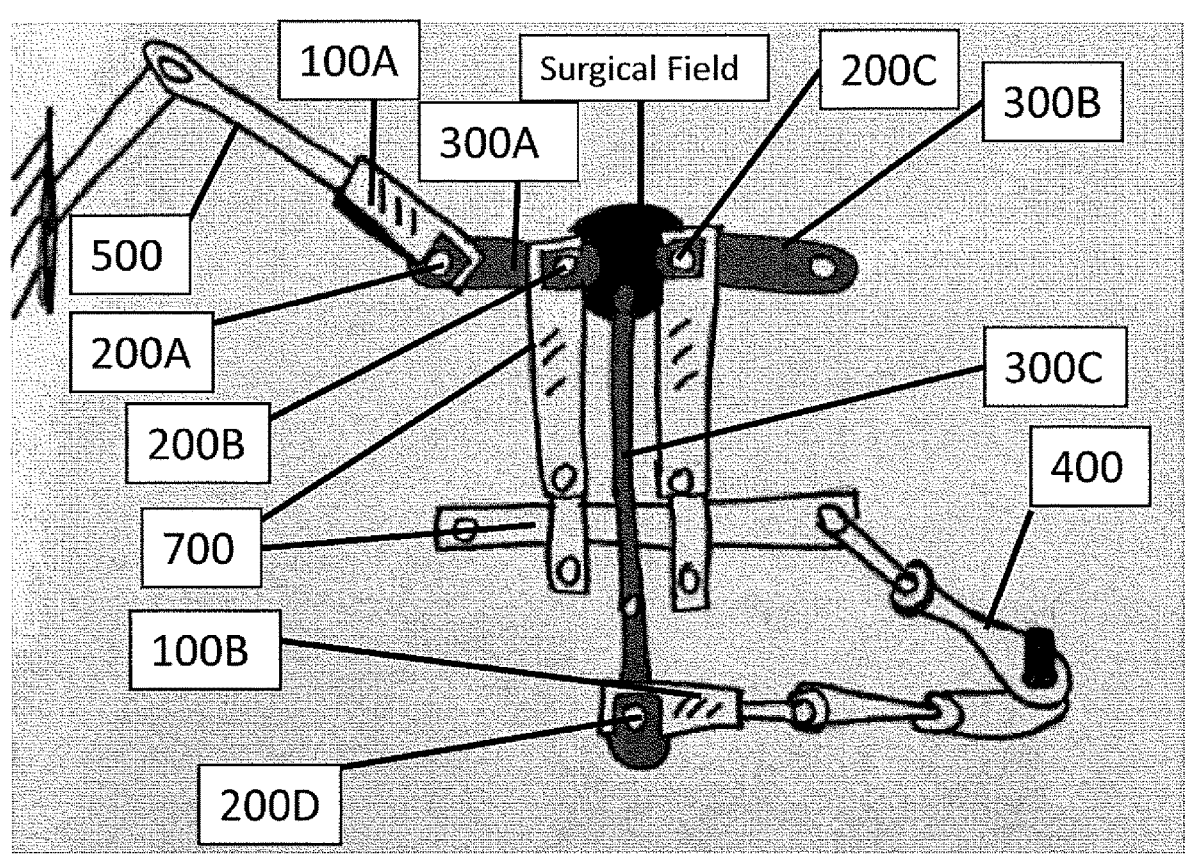
Figure 21:
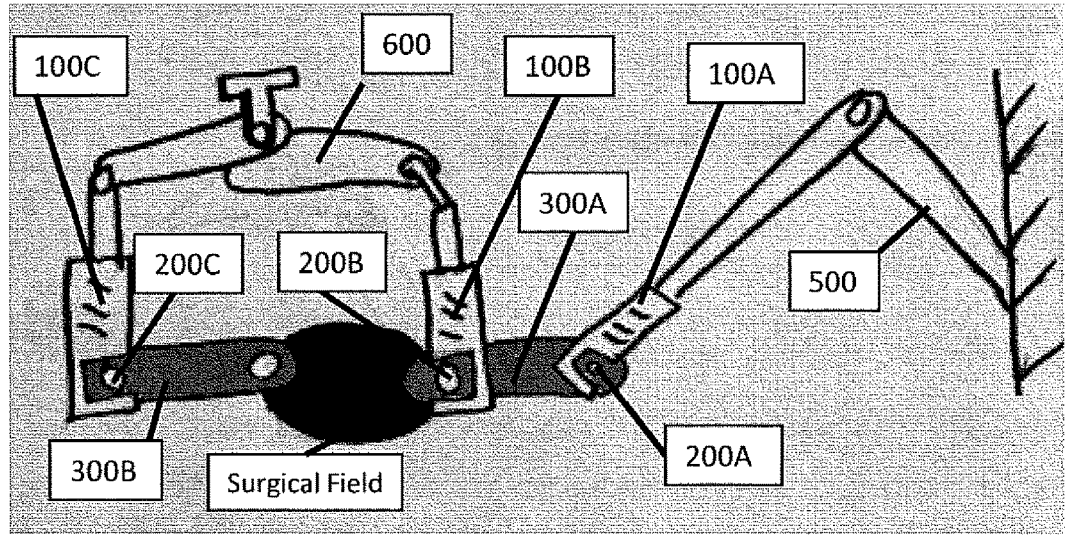
Figure 22:
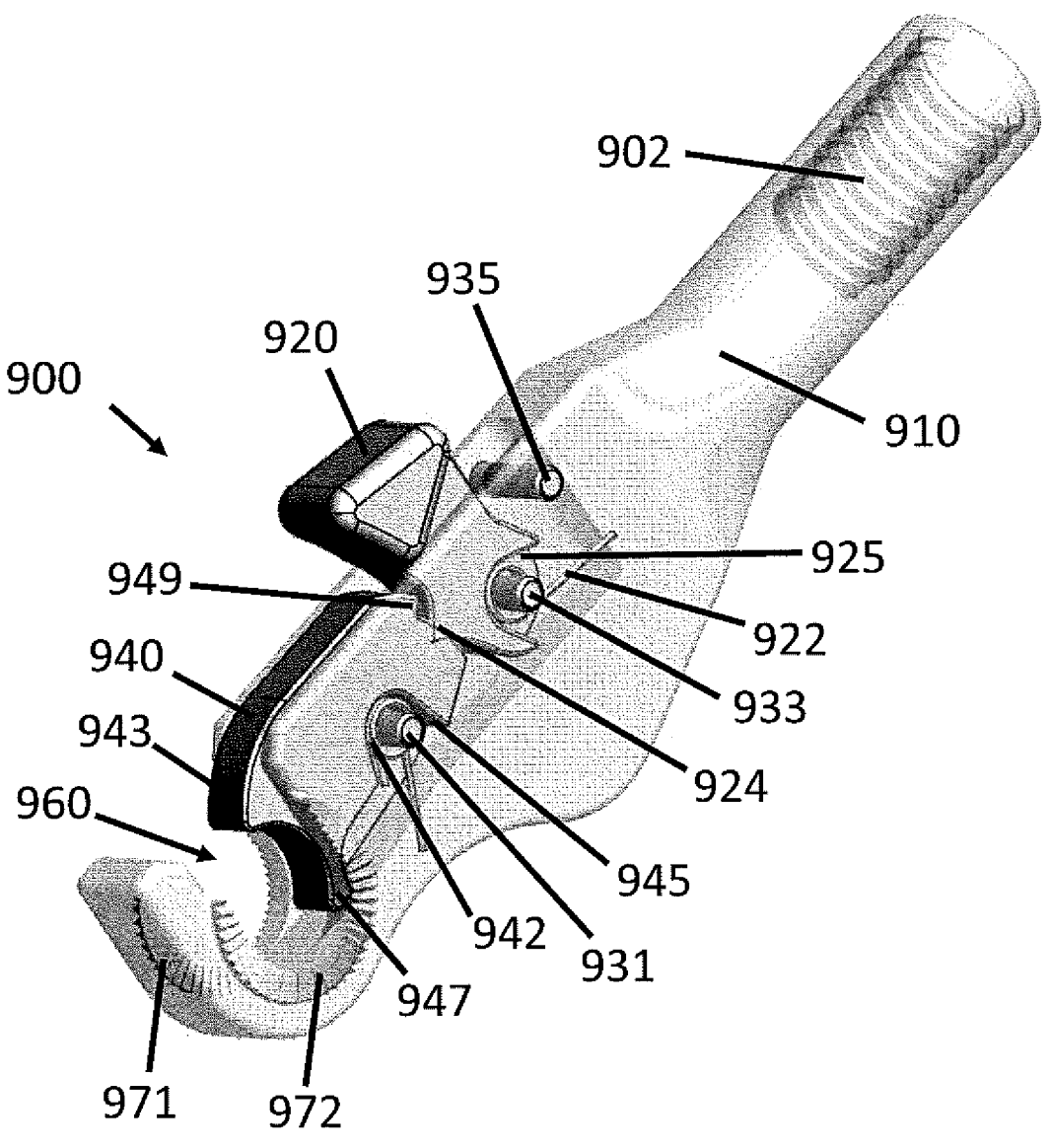
Figure 23:
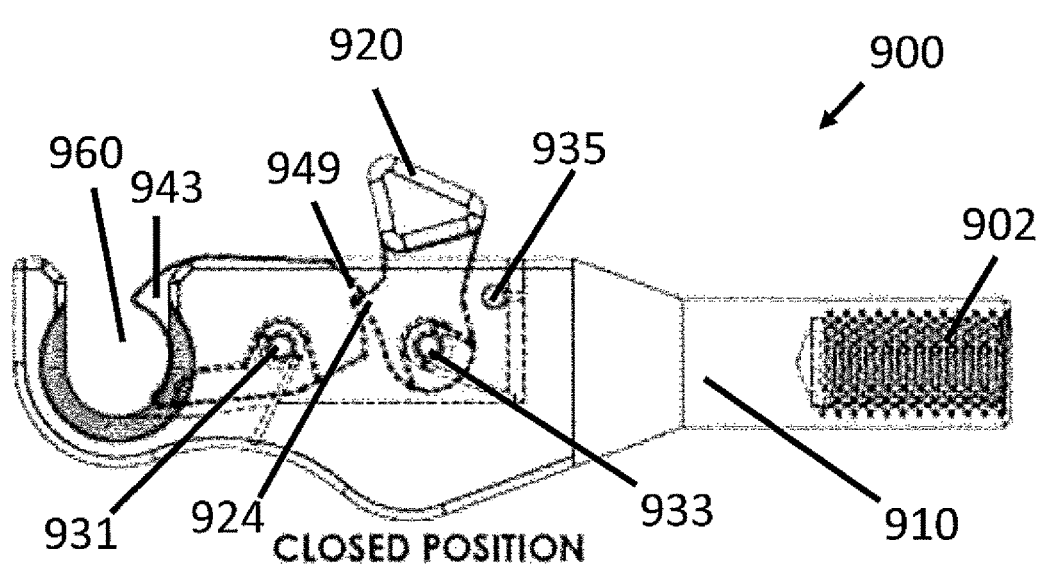
Figure 24:
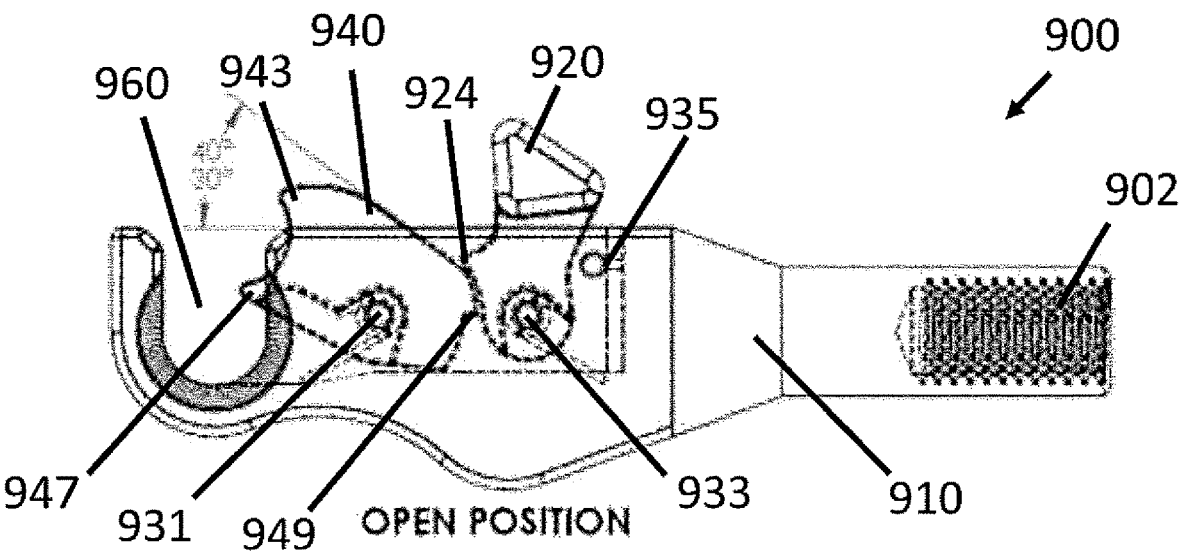
Figure 25:
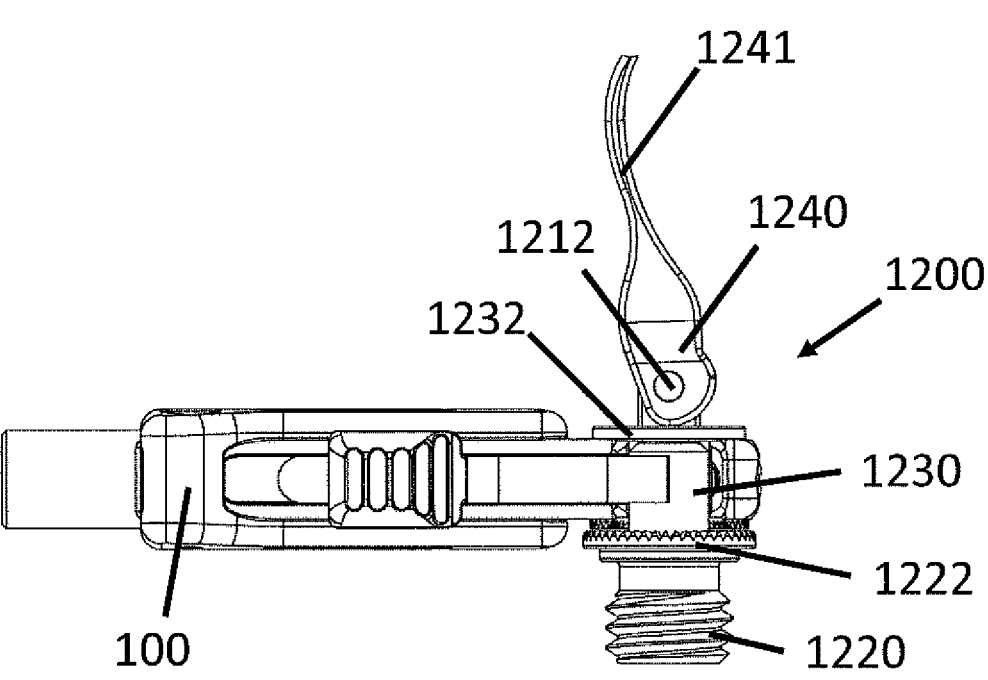
Figure 26:
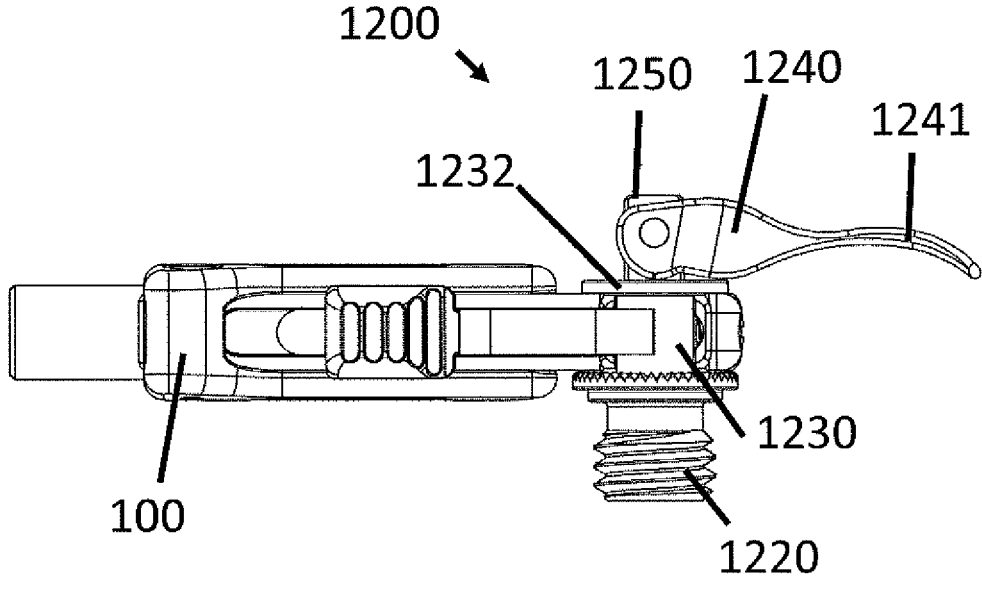
Figure 27:
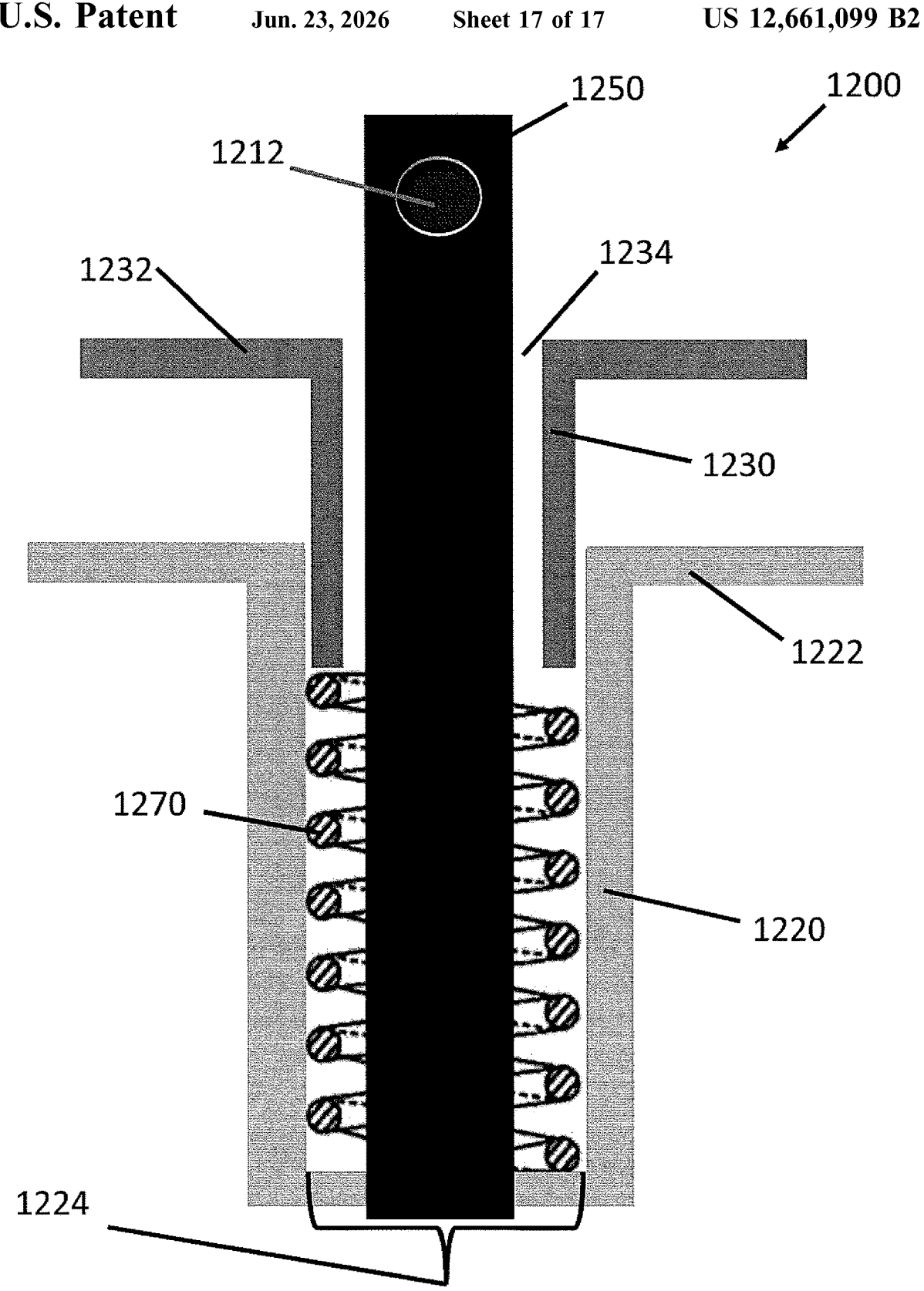

FIG. 3 is a cross-sectional side view of the connector of FIG. 2;

FIG. 4 is an exploded view of the connector of FIG. 2;

FIG. 5 is a perspective view of a table mount arm connector in accordance with one embodiment of the present disclosure;

FIG. 6 is a perspective view of a mini arm in accordance with one embodiment of the present disclosure;

FIG. 7 is a side view of a mini arm in accordance with one embodiment of the present disclosure;

FIG. 8 is a side view of a blade in accordance with one embodiment of the disclosure;

FIG. 9 is an exploded view of the blade of FIG. 8;

FIG. 10A is a side view of a post in the closed position;

FIG. 10B is a side view of the post of FIG. 10A in the open position;

FIG. 10C is an exploded view of the post of FIG. 10A;

FIG. 11 is a side view of a connector attached to a post in accordance with an embodiment of the present disclosure;

FIG. 12 is a close-up view of the connection between the connector and the post of FIG. 11;

FIG. 13 is a perspective view of a combination of a connector and post in accordance with another embodiment of the present disclosure;

FIG. 14 is a view showing a step in a method of attaching a connector to a blade in accordance with an embodiment of the present disclosure;

FIG. 15 is a view of another step in the method of FIG. 14;

FIG. 16 is a view of another step in the method of FIG. 14;

FIG. 17A is a view of the method of FIG. 14;

FIG. 17B is an alternate view of the method of FIG. 14 continuing from FIG. 16;

FIG. 18 is a perspective view of connectors attached and detached from a retractor rack in accordance with an embodiment of the present disclosure;

FIG. 19 is a perspective view of a retractor frame connected to connectors and retraction tools;

FIG. 20 is a top view of a retractor system with a retractor frame in accordance with one embodiment of the present disclosure;

FIG. 21 is a top view of a retractor system in accordance with one embodiment of the present disclosure;

FIG. 22 is a perspective view of a connector in accordance with another embodiment of the disclosure;

FIG. 23 is a side view of the connector of FIG. 22 in the closed position;

FIG. 24 is a side view of the connector of FIG. 22 in the open position;

FIG. 25 is a side view of a connector provisionally attached to a post in accordance with another embodiment of the present disclosure;

FIG. 26 is a side view of the connector of FIG. 25 in the locked position; and FIG. 27 is a cross sectional view of an aspect of the locking mechanism of FIG. 25.

DETAILED DESCRIPTION

As used herein unless stated otherwise, the term "anterior" means toward the front part of the body, and the term "posterior" means toward the back part of the body. When referring to specific directions in the following discussion of a certain device, the terms "proximal" and "distal" are to be understood in regard to the device's orientation and position during exemplary application to human body. Thus, the term "proximal" means closer to the operator or in a direction toward the operator, and the term "distal" means more distant from the operator or in a direction away from the operator. In addition, the terms "about," "generally," and "substantially" are intended to mean that deviations from absolute are included within the scope of the term so modified.

Figure 1:
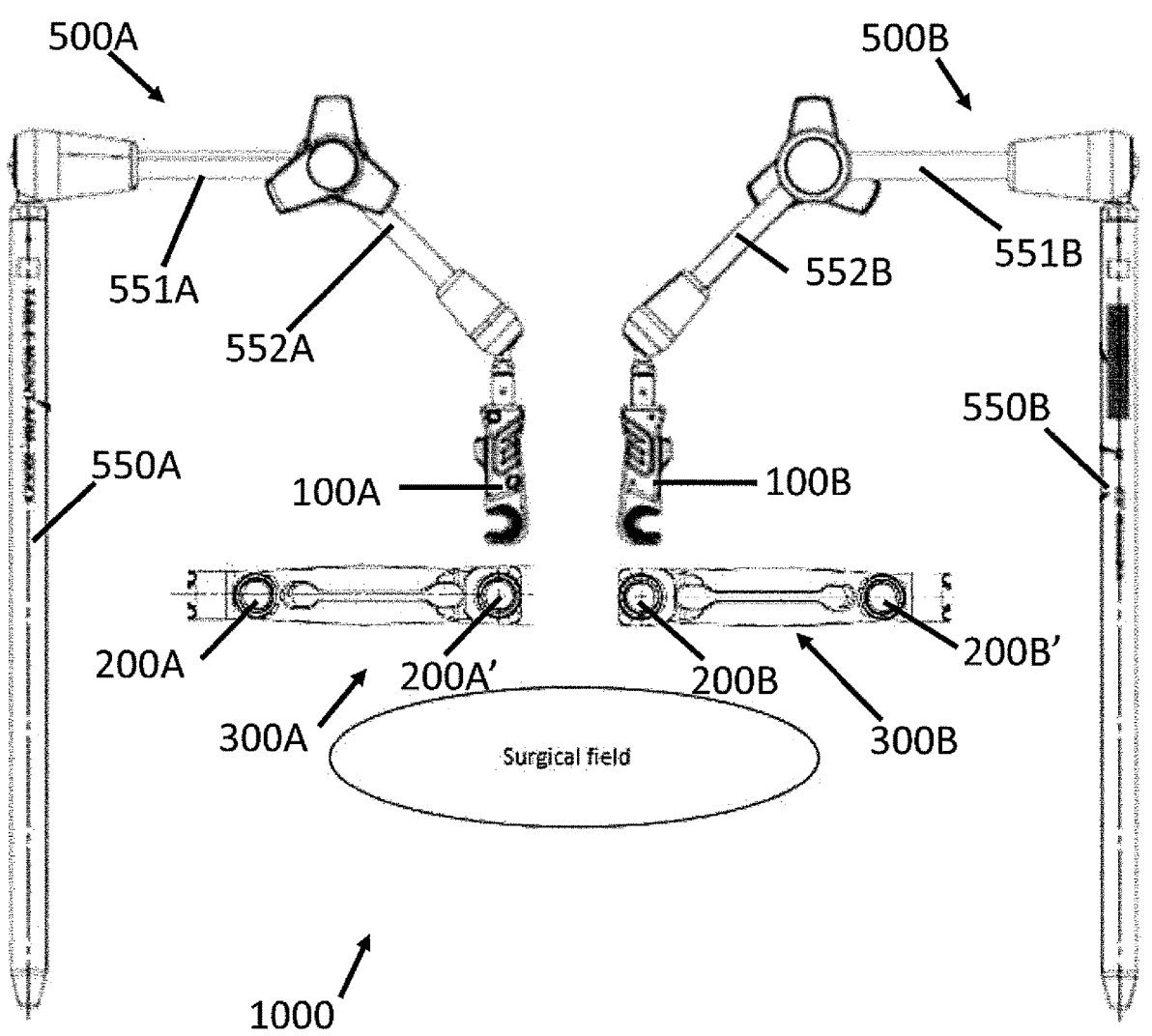
FIG. 1 is a top view of a retractor system in accordance with one embodiment of the present disclosure.

In a first aspect, the present disclosure relates to a connector device. The connector device may be adapted to form a connection end of a support arm structure, such as is shown in FIG. 1, where adjustable arms 500A, 500B include respective connectors 100A, 100B at their respective free ends. This and other arrangements for inclusion of connector 100 in a retractor support system are described in greater detail elsewhere in the present disclosure. It should be appreciated, however, that connector 100 may be used to attach the arm from which it extends to a retractor blade (e.g., blade 300A, 300B) such as that shown in FIG. 1 or to another retractor structure.

In one embodiment, a connector is as shown in FIGS. 2-4 and is indicated by reference numeral 100. Connector 100 includes housing 160, sleeve 163 for housing 160, holder block 110 and bumper block 120. Holder block 110 and bumper block 120 may be disposed in housing 160 in a spring-loaded manner, as shown in FIG. 3. Housing 160 has a length that extends from first end 101 to second end 102. From second end 102, threaded hole 140 extends into an interior of housing 160. Threaded hole 140 is configured to receive a corresponding threaded shaft from, for example, but limited to, mini arm 400, 600, table mount arm 500 or other similar mounting or support devices. Adjacent to first end 101, connector 100 includes receptacle 162. Receptacle 162 extends inward from a side of the housing adjacent to first end 101. As depicted, receptacle 162 has opposing lateral sides 171, 172 facing one another and a curved interior end 173 extending between the lateral sides. The respective lateral sides may be defined by flat edges along the opposing side surfaces of the connector, as shown in FIG. 2. Receptacle 162 is configured to receive an attachment structure of a retractor blade or frame to connect the retractor component to the connector. Such attachment structure may be post 200, for example, described in greater detail elsewhere in the present disclosure. Receptacle 162 may be configured to receive attachment structures having a variety of shapes. For example, receptacle 162 may receive cylindrical shafts, rectangular shafts or triangular shafts.

With continued reference to FIG. 2, housing 160 of connector 100 may also include connector teeth 161A, 161B surrounding receptacle 162 on a side surface of the connector 100. Connector teeth 161A, 161B may be a set of ridges or other projections. Connector teeth 161A, 161B may be located on one or both of the opposing side surfaces of connector 100. Connector teeth 161A, 161B may create a hirth or curvic joint when paired with a set of complementary teeth that similarly shaped to interlock with connector teeth 161A, 161B, such as the teeth on an attachment structure of a retractor blade or frame, described in greater detail elsewhere in the present application. In this manner, connector teeth 161A, 161B allow connector 100 to secure a fixed position relative to a retractor component as connector teeth 161A, 161B firmly interlock with another set of teeth on a retractor component.

Housing 160 of connector 100 may also optionally include adjustment screw 130 which is threaded into receptacle hole 166 (as shown in FIG. 4) at first end 101 of connector 100. Adjustment screw 130 may function as a physical barrier to keep bumper block 120 within receptacle 162, as described in greater detail below. Housing 160 of connector 100 may also include a sleeve or cover. For example, in the region adjacent second end 102 of connector 100, sleeve 163 may be disposed over a core structure of housing 160 and may be anchored to a remainder of housing 160 with a series of fasteners 165, as shown in FIGS. 4 and 6. In other embodiments, the housing may be a single monolithic structure in place of the housing and sleeve combination.

Referring now to FIG. 3, bumper block 120 and holder block 110 are disposed in housing 160. Bumper block 120 is disposed in recess 124 in particular, positioned on bumper spring 122 such that the bumper spring is in between bumper block and an inner surface of the housing. Within recess 124 is a further recess in the form of a dedicated spring recess 125 that receives spring 122, as shown in FIG. 3. Recess 124, larger than the spring recess, is defined by an interior surface shape within housing 160 and above spring recess 125 for receipt of bumper block 120, such that bumper block 120 is disposable over bumper spring 122. One end of bumper spring 122 may be attached to housing 160 within spring recess 125, and the other end of bumper spring 122 may be attached to bumper block 120. The outer surface of bumper block 120 includes concave surface 121 facing an opening of receptacle 162 and configured to match the curvature of third small side 173 of receptacle 162. A shape of concave surface 121 may be varied to accommodate a shape of a post or other engagement feature on a retractor component. Additionally, bumper block 120 may also include grooves 126 to with surface roughening or ridges to provide a more robust gripping surface. The presence of grooves 126 may also increase the likelihood that a post received in the receptacle will contact an apex of the curved surface of bumper block 120. Additionally, the bumper block 120 may have rounded edges to minimize any wear between parts within housing 160.

Holder block 110 is disposed in slot 168 of housing 160 and is oriented along a length direction of connector 100. Holder block 110 includes cavity 117 disposed therein, as shown in FIGS. 3 and 4. Cavity 117 extends through opposing sidewalls of holder block 110. Extending through sides of housing 160 and through cavity 117 of the holder block is pin 113. A holder spring 112 is disposed within cavity 117 such that a first end is in contact with a wall of the cavity and a second end is in contact with pin 113. In some examples, the first end of holder spring 112 is attached to the wall of cavity 117 and the second end is attached to pin 113. In other examples, one or both ends of holder spring 112 may be held in place by the pressure of the spring against the internal wall of holder block 110 and/or pin 113. Holder spring 112 is biased in an expanded state such that when bumper block 110 is retracted and outside of receptacle 162, as shown in FIG. 3, holder spring 112 is in a compressed state. When bumper block 120 is compressed, holder spring 112 is released from its compressed state and pushes tip 116 of holder block 110 into the receptacle. Further details regarding the operation of connector 100 are provided in the description of the methods in the present disclosure. Tip 116 has a curved surface that may be concentric with the curvature of third small side 173 of receptacle 162 and/or concave surface 121. Holder block 110 also includes notch 118 on an inward facing side of the holder block. Notch 118 is shaped and positioned to abut against an outer surface of bumper block 120 when the bumper block is in an expanded position, as shown in FIG. 3. Additionally, holder block 110 may include tab 114 for manually adjusting connector 100 from a closed position (i.e., position where tip 116 is in the receptacle) to an open position (i.e., position where tip 116 is within slot 168). Tab 114 of holder block 110 projects externally relative to a surface of housing 160 of connector 100.

Connector 100 is shown in the open position in FIG. 3. In the open position, bumper block 120 is in an expanded position and may be located in receptacle 162. As stated above, in the open position, an outer surface of the bumper block 120 may hold holder block 110 in place by pressing against notch 118. However, when bumper block 120 is compressed, notch 118 is no longer held in place and holder block 110 is released into receptacle 162. From the closed position of connector 100, tab 114 is slidable toward second end 102 of connector 100 to withdraw holder block 110 from receptacle 162. This action causes bumper block 120 to be released from its compressed position via expansion of bumper spring 122.

In the open position of the connector, bumper block 120 may be prevented from tilting and ejecting out of housing 160 due to abutment against adjustment screw 130 at one location and notch 118 of holder block 110 at another location. In this manner, adjustment screw 130 may aid in retaining bumper block 120 within holder block 160 when the bumper block is in the expanded position.

One or more components of connector 100 may be manufactured together as monolithic structures or as separate components that may be assembled. Components of connector 100 can be manufactured from various plastics, metals, metal alloys, or any combination thereof. For example, bearing components such as receptacle-facing components of the connector and a post may be made of steel or titanium.

In a second aspect, the present disclosure relates to an arm structure that includes a connector, such as connector 100. In some embodiments, connector 100 may be part of an arm structure so that the arm structure has connector 100 at one end and either a rigid support or another connection end at another end of the arm. Examples of such embodiments are shown in FIGS. 5-7. In FIG. 5, connector 100 may be part of a rigid arm, e.g., a table mount arm 500. Table mount arm 500 includes arm segments 550, 551, 552 and 540. An end of arm segment 540 includes a threaded tip (not shown) for receipt in threaded hole 140 of connector 100. In this manner, connector 100 is secured to arm segment 540 via a threaded connection. Each arm segment is connected to an adjacent arm segment via a joint. Arm segments 550 and 551 are connected via articulating joint 511. As depicted in FIG. 5, articulating joint 511 is a ball-and-socket joint with partial freedom of movement, a housing over segment 551 restraining rotation of segment 550 out of a plane passing through segments 550 and 551. In other examples, the joint may be structured differently to provide lesser or greater restriction on movement. Arm segments 551 and 552 are connected via articulating joint 520. As depicted, joint 520 permits rotational movement of arm segment 552 relative to arm segment 551 in a single plane, i.e., in a hinge-type action. Handle 521 may be configured to loosen and tighten the joint between an open position where the rotational position of the arm segments may be adjusted to a locked position where the relative position of the arm segments is preserved. Arm segments 552 and 540 are connected via articulating joint 510. As depicted, joint 510 is a ball and socket joints that provides for full rotational freedom of movement of segment 540 relative to arm segment 552. Joints 510 and 511 may include a locking feature to loosen and tighten the respective joints to control whether a position of the arm segments is adjustable. When locked, respective articulating joints, 510, 511, and 520 maintain adjacent arm segments in a rigid position with respect to each other. Arm segment 550 or optionally an additional arm segment upstream of segment 550 may be configured to be secured to a stationary table or other fixed location or support in an operating room such that table mount arm 500 is firmly anchored.

In some embodiments, an arm structure may be in the form of a mini arm assembly, such as mini arm assemblies 400, 600 shown in FIGS. 6 and 7, respectively. Mini arm assembly 400 includes central joint 420 and sub-arm components 451A and 451B, each extending from the central joint. Sub arm components 451A, 451B are rotationally attached to central joint 420 at a first end, and sub arm component 451B is attached to an enclosed connector 460 at a second end. Sub arm component 451B and enclosed connector 460 form a ball and socket joint 410B, which may have a similar structure to ball and socket joint 510 in FIG. 5. A free end of enclosed connector 460 may be threaded onto connector support shaft 440B and includes central base 430. Central base 430 may have a hollow cylindrical shape for receipt of a securement feature of a retractor component. In FIG. 6, such securement feature is post 200. Post 200 may be threaded into central base 430 via internal threads on the central base, for example. Further details of how post 200 is used on a retractor structure are described in greater detail elsewhere in the present disclosure. Sub arm component 451A is rotationally attached to central joint 420 at a first end and extends to a second end where sub arm component 451A is attached to connector support shaft 440A. Connector 100 is threaded onto connector support shaft 440A, in a manner similar to the embodiment shown in FIG. 5. Sub arm component 451A and connector support shaft 440A form a ball and socket joint 410A, similar to ball and socket joint 410B. Each joint 410A, 410B may be locked and unlocked in a similar manner to that described for such joints in arm 500. Central joint 420 may include, as shown in FIG. 6, a screw top feature that may be tightened or loosened to allow or prevent movement between sub-arm components 451A and 451B.

Mini arm assembly 600 is shown in FIG. 7. Reference numerals of the 600 series of numerals refer to like elements in the 400 series of numerals, unless otherwise noted. Mini arm assembly 600 includes two sub arm components 651A, 651B, each with the same features as sub arm components 451A and 451B of mini arm assembly 400. Both sub arm components are moveable with respect to central joint 620 in the same manner as in assembly 400.

It is contemplated that connector 100 may be connected to table mount arms 500 and mini arm assemblies 400, 600 that vary in length and design from what is shown in the figures.

In a third aspect, the present disclosure relates to retractor components for use in surgery where such components include an attachment structure for engagement with a connector, such as connector 100. Such retractor components may be a retractor blade as shown in FIGS. 8 and 9 or a retractor frame as shown in FIGS. 18 and 19, for example.

With reference to retractor blade embodiments in particular, one embodiment of a blade with one or more attachment structures, indicated by reference numeral 300, is shown in FIGS. 8 and 9. Hand-held blade 300 includes blade portion 320 and handle portion 310. Blade portion 320 is configured to be inserted into the surgical area and retract tissue. Handle portion 310 includes first hole 331 and second hole 332. An inner surface of the first and second holes is threaded. Further, each hole is sized to receive an attachment structure in the form of a post 200, described in greater detail below. As depicted in FIG. 9, hand-held blade 300 may have one post 200 in either first hole 331 or second hole 332. Alternatively, the hand-held blade may include posts 200 received in respective holes 331, 332 of handle portion 310. In some variations, handle portion 310 may include only one of the first hole and the second hole. And, in some variations, the hand-held blade may be fabricated with the post or posts (e.g., post 200). In a subset of such variations, the post or posts may be integral with the handle of the hand-held blade. As described elsewhere in the present disclosure, one or more connectors 100 may be attached to one or more hand-held retractor blades to form a system.

In other embodiments, a retractor frame with one or more attachment structures may be as shown in FIG. 19. Retractor frame 700 includes a retraction bar 710 that extends from a first end to a second end. Disposed along retraction bar 710 are translatable arms with blades attached thereto. As shown in FIGS. 18 and 19, adjacent to each end of retraction bar 710 are posts 200. In some variations, retraction bar 710 may include a single post at either end or at another location along the bar. And, in some variations, retraction bar 710 may be fabricated with the post or posts. In a subset of such variations, the post or posts may be integral with retraction bar 710. As described elsewhere in the present disclosure, and as shown in FIGS. 18 and 19, one or more connectors 100 may be attached to retractor frame 700 to form a system.

Post 200 is shown in isolation in FIGS. 10A-10C. For the sake of brevity, the depicted embodiments are described with reference to post 200, although it should be appreciated that the attachment structure is not limited to the depicted embodiment. Post 200 is complementary to connectors 100 described in the present disclosure and may be operatively connected therewith. Post 200 includes top portion 210, shaft 230 extending therefrom and base portion 220 threadably engageable over shaft 230. Top portion 210 is a knob-like component atop the post 200. Top portion 210 is configured to receive shaft 230. Post pin 212 may be disposed through an opening in top portion 210 and shaft 230 to fix top portion 210 to shaft 230. Top portion 210 and shaft 230 are configured to receive post pin 212 through pin holes 211 and 231, respectively. In some variations, top portion is integral with shaft. Base portion 220 has a generally cylindrical shape with a threaded exterior surface 222, an upper annular lip 225 and a lumen 224 extending longitudinally therethrough. A surface of upper annular lip 225 facing away from a remainder of base portion 220 may include annular post teeth 226 as shown in FIG. 10C. As described elsewhere in the present application, post teeth 226, 216 may engage with complementary annular teeth on a connector, such as annular connector teeth 161A, 161B, to provide a rotational fixation between the element associated with the post and the connector. An interior surface defining lumen 224 may be threaded to facilitate threaded engagement between base portion 220 and shaft 230. In some variations, a shaft-facing end of top portion 210 may include annular post teeth 216.

FIG. 10A shows post 200 in the closed position with no space between top portion 210 and base portion 220 such that post teeth 216 and 226 are interlocked. As mentioned above, post teeth 216 and 226 may be configured to interlock with connector teeth 161A and 161B which may have a sharp jagged shape or a blunt shape. FIG. 10B shows post 200 in the open position indicated by the distance between top portion 210 and bottom portion 220 that exposes shaft 230. When bottom portion 210 is held or otherwise secured to a retractor component, post 200 is adjustable from the closed position (as shown in FIG. 10A) to the open position (as shown in FIG. 10B) through rotation of top portion 210 in a counterclockwise direction such that shaft 230 is screwed out of the base portion 220. A reverse rotation of top portion 210 (i.e., clockwise) moves post 200 from the open position into the closed position. It should be appreciated that an object (e.g., connector 100) can be placed between base portion 220 and top portion 210 with the top portion 210 screwed down tight against the object. In such instances, post 200 is considered in the closed position when top portion 210 engages and clamps down against such object. This is shown, for example, by engagement between post 200 and connector 100 in FIGS. 11 and 12. In a variation, the post may have threading oriented such that a direction of rotation to move between the closed and open positions is reversed.

To avoid ambiguity, it should be appreciated that post 200 as shown in FIGS. 10A, 10B, and 10C may be used or included with a hand-held blade such as blade 300 shown in FIG. 9 or retractor frame 700 as shown in FIG. 19.

FIG. 13 shows an alternative embodiment of a connector and blade structure. Connector 840 includes a receptacle 845, annular teeth 844 surrounding the receptacle, a button 841 and a holding block 843. Connector 840 may include a button 841 operatively connected to holding block 843. In some examples, actuation of button 841 causes release of the holding block 843 into receptacle 845. The holding block may be disposed within the connector such that its release causes it to pivot into the receptacle or to translate into the receptacle. The operative connection between the button and the holding block may include a spring or spring-like mechanism such that the button releases a pin or other holding structure that causes the spring to expand into its biased condition. To withdraw holding block 843 from the receptacle into a cavity of the connector body, the holding block may simply be translated or rotated back into its withdrawn position and may be set in place by snapping in a surface feature on the holding block with a complementary feature within the connector body. Such feature would be the pin or other holding structure mentioned above. In other examples, ratchets and other mechanisms may be included in the operative connection between the button and the holding block.

Surgical tool 800 further includes blade 870 and extension shaft 880 extending from the blade with hub 890 receiving a rotatable knob 820 therein. Optionally, and as shown in FIG. 13, an end of the extension shaft opposite blade 870 includes ball 830 of a ball and socket joint. At a base of shaft 850 there may be an annular distribution of teeth 860. Shaft 850 is sized to receive receptacle 845 of connector 840. Knob 820 may be screwed in and out of surgical tool 800 to control locking of connector 840 when the connector is disposed over the shaft. Exposed ends of shaft 850 may both include teeth to complement and interlock with teeth 844 on connector 840 to provide rotational fixation when knob 820 is rotated into a locked position with connector 840. A provisional connection is made once shaft 850 is received by receptacle 845 and button 841 is subsequently triggered to release spring-loaded holder block 843 to engage shaft 850. Tightening of knob 820 may rigidly fix the components. It is contemplated that teeth 844 may be disposed on both sides of connector 844. In another aspect, the present disclosure relates to systems that include at least one connector and at least one retractor blade or retractor frame configured to be operatively connected to such connector. In one embodiment, a system 1000 includes two rigid arms 500A, 500B with respective connectors 100 for connection with hand-held blades 300, as shown in FIG. 1. Connectors 100A, 100B are configured to attach to rigid arms 500A. 500B by, for example, a threaded connection. Rigid arms 500A, 500B have articulating joints (e.g., ball and socket joints) that allow for movement between sub-arm components 550A-B. 551A-B, 552A-B while in a loosened state. Once tightened, the articulating joints become fixed to a particular rotational position. Additionally, rigid arms 500A, 500B are configured to attach and to a sturdy structure (e.g., a table or wall) to anchor the arms. Further details regarding rigid arm 500A, 500B details are provided elsewhere in the present disclosure. Connectors 100 are configured to provisionally connect with a post 200 disposed on hand-held blades 300A, 300B. Hand-held blades 300A, 300B may contain multiple posts. For example, in system 1000, connectors 100A, 100B can be connected to any combination of two posts from among posts 200A, 200B, 200A', 200B'. It is contemplated that system 1000 may alternatively include only one rigid arm, one connector, and one hand-held blade.

In another embodiment, a system may include a rigid arm and a retractor frame. A connector of the rigid arm is configured to attach to a post on a retraction bar of the retractor frame. In one example, this may be connector 100 on a rigid arm 500 attached to a post 200 on retraction bar 710 of retractor frame 700. In some examples of this embodiment, the system may include two rigid arms, the retractor frame and a hand-held blade. A connector on the second rigid arm may be configured to attach to a post on the hand-held blade. The hand-held blade may be blade 300.

In some embodiments, a system may include a rigid arm, a mini arm assembly, and one or more hand-held blades. In one example of this embodiment that includes two hand-held blades, a connector of the rigid arm is configured to attach to a first post on the first hand-held blade. Further, the mini arm assembly (e.g., mini arm 600) is configured to attach a second post of the first hand-held blade to a post of the second hand-held blade. It is also contemplated that the mini arm assembly, such as mini arm assembly 400, may be connected to the rigid arm as an extension between the rigid arm and a hand-held blade.

In still further embodiments, a system may include a rigid arm, a retractor frame, a mini arm, and one or more hand-held blades. In one example, two blades with at least two posts disposed thereon (e.g., hand-held blades 300) are connected to the retractor frame. The rigid arm is configured for attachment to one of the blades connected to the retractor frame thereby providing support for the retractor frame. The mini arm (e.g., mini arm 600) is then connected to the retractor bar of the retractor frame and a third blade. It is contemplated that the mini arm in this example may be connected to another type of retraction tool. In other examples of the above embodiments including a retractor frame, the retractor frame may include one or more blades solely supported by an arm of the retractor frame in place of a dual-use hand-held blade.

In some embodiments, a system may include a hand-held blade and a rigid arm. In other embodiments, a system may include two rigid arms and two hand-held blades. In further embodiments, a system may include three rigid arms and three hand-held blades. In some examples, each rigid arm is configured for attachment to a respective hand-held blade of the system via attachment of a connector and a post.

In another aspect, the present disclose relates to a kit that may include retractor components in a single package or in multiple packages that may be selected as needed by a surgeon to form a system. Such kits may be very basic including only one or two connectors or such kits may include a larger variety of surgical tools. In some embodiments, a kit may include two or more blades each having at least one post. In other embodiments, a kit may include two or more connectors and two or more blades each having at least one post. In any of the above embodiments, a connector may be part of a rigid arm or a mini arm assembly. In other embodiments, a kit may include at least one connector 100, at least one support arm 400, and at least one hand-held blade 300. Hand-held blade(s) and support arm(s) may be any blade or support arm described herein or otherwise contemplated.

In another example, the kit may include two or more connectors 100, two or more support arms 400, and two or more blades 300. In such examples, connectors may be part of support arm(s) or retractor frame(s) or mini arm(s) included in the kit. It is contemplated that these kits may include tools of varying sizes and designs. It is also contemplated that the above kits may be further modified to include other surgical tools used in conjunction with the hand-held blades such as retraction instruments. In some of the examples above, the kits contemplated may be accompanied by an instruction manual on how to perform one or more of the methods of using the contents of the kit.

In yet another aspect, the present disclosure relates to a method of assembling connector 100. With reference to FIGS. 3 and 4, connector 100 may be assembled by first inserting bumper spring 122 into spring recess 125 and bumper block 120 into larger recess 124 above spring recess 125 such that bumper spring 122 is seated between and connected to bumper block 120 and housing 160. Holder spring 112 is disposed in cavity 117 of holder block 110, and holder block 110 is inserted into slot 168. Pin 113 is then passed into housing 160 such that one end of holder spring 112 is in contact with pin 113 and the other end of holder spring 112 is in contact with an inner wall of holder block 110. Once inserted, pin holes 119 in holder block 110 are aligned with holes 164 in housing 160 such that pins 111 may be received therethrough. Additionally, adjustment screw 130 may be threaded into receptacle hole 166. Optionally, an outer sleeve 163 may be mounted on the exterior of connector 100 to provide grip for the user. Outer sleeve 163 may be mounted via pins 165.

In yet another aspect, the present disclosure relates to a method of connecting a connector and a post together. One example of the connection between connector 100 and post 200 is shown in FIGS. 11 and 12. When post 200 is in the open position, receptacle 162 of connector 100 may receive shaft 230 of post 200. When shaft 230 presses against bumper block 120 to push the bumper block further into recess 124, notch 118 becomes disengaged from the bumper block. This causes spring 112 to be released such that holder block 110 is drawn into receptacle 162, with tip 116 of holder block 110 extending into receptacle 162 until the curved surface of tip 116 abuts shaft 230 of post 200. This provides a provisional attachment between post 200 and connector 100. With provisional attachment between connector 100 and post 200, the retractor component connected to the post via base 220 may be rotated while the connector supports the post to prevent displacement of the post relative to the connector. The retractor component may be a handheld blade or a retractor frame, for example. From the provisional attachment position where holder block 110 and bumper block 120 are in contact with shaft 230 on substantially opposite sides, top portion 210 of post 200 may be used to arrive at a fixed position between the connector and the post. Upper portion 210 is rotated and as a length of exposed shaft 230 decreases and approaches a thickness of connector, annular teeth on the post engage with annular teeth on the connector to create a hirth joint. For example, teeth 226 on base portion 220 of the post engage with connector teeth 161A on a side of the connector. FIG. 12 shows a close-up of an example with two sets of interconnecting teeth: one on a top side of the connector and another on the bottom side, each forming a hirth joint. Once upper portion 210 is rotated sufficiently to arrive at a tight fit on the connector, the connector and the post have a fixed attachment such that relative rotation or any other relative movement between such components is restrained.

With continued reference to the above example, the method may further include an optional step of adjusting the post so that the attachment reverts from a fixed attachment to a provisional attachment. Connector 100 may be repositioned with respect to shaft 230 by unscrewing or loosening (i.e., rotating counterclockwise) the top portion 210 of the shaft such that post teeth 226, 216 and connector teeth 161A, 161B are unlocked as they move apart from each other as shaft 230 is rotated or screwed out of base portion 220. In this loosened state, there remains a provisional connection between connector 100 and post 200 which allows connector 100 to rotate or shift slightly with respect to post 200 and/or vice versa. The degree of available movement may be a function of how much the top portion 210 of the shaft is loosened.

In other embodiments of the method of use, a method involves connecting various surgical tools together. In this manner, a mini arm 400, 600 or a support arm 500 with a connector 100 at a respective free end may be connected to a post 200 on a hand-held blade 300 or a retractor frame 700. In some examples, this method may be performed for two or more supporting arm instruments, each being attached to a respective retraction tool, such as a hand-held blade or retractor frame.

In further embodiments of the method, the method may include using a support arm with a connector and one or more retraction tools to access a surgical site. In some embodiments, the method may further include steps for the creation of a surgical access portal. In some examples, the method may include preliminary steps and creation of surgical access steps. For example, the preliminary steps may include but are not limited to: positioning the patient; identifying an incision location based on the surgical target; and cutting through tissue layers to create an initial opening or portal for accessing to the surgical site. Any number of the aforementioned steps may be performed as part of the method, along with additional steps.

In one example, a method for using connector 100 when accessing a surgical site is shown in FIGS. 14-16. This method may include one or more of the preliminary steps as stated above. Then, two hand-held blades 300 may be advanced into patient, either simultaneously or in sequence. Once advanced into the patient, one or both of the blades may be retracted 10A, 10B or otherwise adjusted to create a desired access pathway location and size. As shown in FIG. 14, once the blades are in a suitable position within the access, support arms (not shown) including connectors 100 at their respective ends are advanced to each blade 300. As shown in FIG. 15 for one representative blade 300, a receptacle of connector 100 is then engaged to a respective post 200 on the blade, thereby creating a provisional attachment between the two. This process is advantageous in that a single user may perform this step simply by holding the blade with one hand and holding the support arm with another hand. At this juncture, the blade may be rotated to a desired orientation relative to the arm, then, as shown in FIG. 16, top portion 210 of post 200 may be actuated by rotating top portion 210 such that the post becomes fixed relative to connector 100. When top portion 210 is rotated sufficiently, top portion 210 presses against the connector and connector teeth 161A and 161B interlock with post teeth 226 and 216, respectively.

In variations of the example described above and shown in FIGS. 14-16, the method may also include one or both of the additional steps shown in FIGS. 17A and 17B. This variation may also be a standalone method. FIG. 17A shows adjustment of a position and orientation of support arm 500 (of which connector 100 is shown in FIG. 17) while hand-held blade 300 is fixedly attached to the arm. Additional details for support arm 500 with a connector end 100 are shown in FIG. 5. Adjustment of the support arm may be accomplished in several ways. For example, arm segments may be adjusted via one of the ball-and-socket joints and/or the central joint in the support arm, as described elsewhere in the present application.

In a further optional step, a fixed attachment between retractor blade or retractor frame to a connector of a support arm may be returned to a provisionally attached condition. As shown in FIG. 17B, with hand-held blade 300 advanced into the patient and positioned, top portion 210 of post 200 may be loosened by rotating counterclockwise such that connector 100 and hand-held blade 300 return to a provisionally attached condition. And, once in such a state of attachment, shaft 230 of post 200 on the hand-held blade 300 can be rotated between holder block 110 and bumper block 120 without escaping receptacle 162 of connector 100. Such function amounts to an ability to rotate hand-held blade 300 with respect to support arm 500. And this rotation allows hand-held blade 300 to be repositioned after initial placement without risking complete disconnection between hand-held blade 300 and support arm 500. Once hand-held blade 300 has been repositioned, top portion 210 of post 200 may be tightened again to reengage connector teeth 161A. 161B with post teeth 226, 216 and to grip the connector via top portion 210 of post 200.

In some alternative examples of the access creation steps, hand-held blade 300 is provisionally connected to support arm 400 via connector 100 before hand-held blade 300 is advanced into the patient. Hand-held blade 300 is then positioned within the receptacle of the connector, and this position is then secured by tightening top portion 210 of post 200 onto the connector to form a hirth joint or curvic coupling. From this point, the blade is advanced into the initial incision of the patient for purposes of tissue retraction. In some variations of this example, a second blade may be arranged in the same way and then advanced into the patient. In further variations, a second blade may be inserted by hand and then attached to a support arm after being positioned within the patient. The attachment of the blade to the arm before insertion into the patient may be a step incorporated as a variation of any contemplated method involving the use of any system contemplated by the present disclosure.

Other examples of the method involving attachment of a connector to a post involve the use of a retractor frame as part of the procedure, such as system 1100 shown in FIGS. 18 and 19. In FIG. 18, a connector 100A on a support arm (not shown) is advanced to and attached to post 200A on retractor bar 710 of retractor frame 700. In one example, retractor frame 700 may include a pair of translatable arms with blades attached, as shown in FIG. 19. Optionally, and as shown in FIGS. 18 and 19, a second arm with connector 100B may also be advanced to the frame for connection to a second post 200B on frame 700. The second arm may be a mini arm assembly, such as mini arm assembly 400, 600, or it may be another support arm. Where the second arm is a mini arm assembly, an end of the assembly opposite that connected to retractor frame 700 may be attached to a hand-held blade, such as blade 300 (not shown in FIGS. 18 and 19). For each connection to frame 700, connectors 100 are initially provisionally attached to retractor bar 710 as shown in FIG. 18. This is done by advancing the receptacles of the respective connectors 100A, 100B onto posts 200A, 200B along the retractor bar 710, thereby snapping the connectors into place and forming a provisional attachment at each post. Once provisionally attached, the posts 200A, 200B may be tightened to arrive at a fixed attachment between the connectors 100A, 100B and the retractor bar 710. Once supported (e.g., from a rigid arm) through the fixed attachment, the retractor frame 700 may be connected to other blades and retraction tools before or after such tools are advanced into a patient. Hand-held blades 300 may be substituted for the blades shown in FIG. 19, either from the outset or as replacements for those blades during use. Additionally, it is contemplated that in some examples, a system may include one or more connectors 100 that are integral with retractor frame 700.

In another embodiment, a method of creating access to a surgical site may involve the use of retraction and support instrumentation as shown in FIG. 20. In this method, various components including a retractor frame, blades, mini arm, and table mount arm may be all connected together to aid in the creation and maintenance of access to a surgical field. In this arrangement, blades 300A, 300B may be initially inserted into the access portal by hand. Both blades 300A and 300B may be positioned opposite to each other. Then, arms on retractor frame 700, each including connectors with receptacles at their distal ends, may be snapped into place onto posts on the respective blades. In FIG. 20, such attachment is made at posts 200B, 200C. Either of blades 300A, 300B may include a handle with two posts thereon. In this manner, table mount arm 500 may be connected to hand-held blade 300A even when blade 300A is already attached to retractor frame 700. Such connection may be made via attachment of connector 100A on the arm to post 200A located at a proximal end of the handle on the blade. This is done by snapping a receptacle of connector 100A onto post 200A. If both of the above attachments are made, both retractor frame 700 and blades 300A, 300B are held in position via table mount arm 500. Optionally, mini arm 400 may connect to retractor frame 700 at one end and to blade 300C through attachment of connector 100B with post 200D. The above attachments between instrumentation may be performed in any order and the above is merely illustrative. Further, an initial attachment between components may be initially provisional with an allowance for rotational movement between connected components. Connections between the various blades and connectors may be fixed by rotating a top portion 210 knob-type structure of the posts to lock the post to the connector. In this manner, the table mount arm may support a retractor frame, three blades, and a mini arm.

In yet another embodiment, a method of creating access to a surgical cite may include table a mount arm, a mini arm and blades, as shown in FIG. 21. For example, table mount arm 500 may be mounted to a wall or fixed surface and then connected to blade 300A through attachment of connector 100A to post 200A. In this instance, blade 300A would be positioned in the surgical field before its position is secured. Additionally, mini arm 400 may connect to blade 300A through connector 100B and post 200B at one end. The other end of mini arm 600 may be connected to a second blade, blade 300B through attachment of connector 100C to post 200C. Before fixing the attachment locations via the rotatable top portion of the posts, one or both of blades 300A, 300B may be placed and/or adjusted within the surgical site.

The methods disclosed above may be varied in many ways. Various retraction tools such as Hohmann blades, manual lipped blades, other blades such as those shown in FIG. 19, retractor frames, among others, may have post 200 disposed thereon, where such posts 200 are configured for attachment to connector(s) 100. For example, lipped blades have a lip disposed at the end of the blade portion such that the blade portion extends vertically from the handle portion with an end portion that curves back in the direction of the handle portion, as shown in FIGS. 8-9. This lip feature allows for the lipped blade to hook and hold matter within surgical sites. On the other hand, Hohmann blades have a narrow tip at the end of the blade portion that slightly bends away from the handle portion. Other manual blades may come in a variety of designs, like the manual blades in FIG. 19 that have a vertically oriented concave blade portion. Additionally, a variety of mounting tools (e.g., mini arms, table mount arms, support mounts, etc.) with different sizes and designs may be configured to connect to connector(s) 100 by a threaded connection. Such mounting tools may also optionally have post(s) 200 disposed thereon so that they may be provisionally connected to and interlocked with another connector(s) 100. The retractor frame then connects to two blades that are inserted into a surgical site. These examples show that post 200 may be disposed on a variety of surgical tools to facilitate connection with connectors 100.

FIGS. 22-24 illustrate an alternative embodiment of a connector. Connector 900 may include housing 910, lever 920, lever spring 922, lever pin 933, spring-loaded holder block 940, holder block spring 942, holder pin 931, and housing pin 935. Housing 910 includes receptacle 960, and annular teeth 971, 972 therearound on opposing side surfaces of the housing. Housing 910 may be configured to house all the components of connector 900 internally, such that components of connector 900 are at least partially disposed within a cavity of housing 910. One end of housing 910 may include a threaded attachment 902 that extends from housing 910. Spring-loaded holder block 940 may include a first end with flange 949 and a second end with jaws 943, 947. Spring-loaded holder block 940 may be secured within housing 910 by holder pin 931 with coil spring 942 wrapped therearound such that the second end of holder block 940 faces receptacle 960. Lever 920 may include lip 924 sized and positioned to be operatively engageable with flange 949 of block 940. Lever 920 may be secured within housing 910 by lever pin 933 with coil spring 922 wrapped therearound such that spring-loaded holder block 940 and lever 920 are operatively connected to each other with holder block 940 being in between the receptacle and lever, as shown in FIG. 22. Each of holder block 940 and lever 920 are pivotable about the pins upon which they are disposed. Holder spring 942 may be disposed interior to holder groove 945 such that holder pin 931 is placed through holder spring 942. Lever spring 922 may be disposed interior to lever groove 925 such that lever pin 933 is placed through lever spring 922. The respective grooves are recessed regions within the respective rotating components. Each of holder spring 942 and lever spring 922 may be configured to have two substantially straight portions that extend from opposite ends of the spring coil. Additionally, holder spring 942 and lever spring 922 may wrap around holder pin 931 and lever pin 933, respectively, to create a secure connection. In the depicted embodiment, the springs may be configured such that spring-loaded holder block 940 is biased in the open position (as shown in FIG. 23) and lever 920 is biased in the closed position (as shown in FIG. 24). Through this configuration, the holder block and the lever push against each other while in the open and closed positions, thereby maintaining those positions until an external force is applied. In this manner, lever spring 922 holds connector 900 in the closed position and holder spring 942 holds connector 900 in the open position until an external force overcomes the respective spring forces.

FIG. 23 shows connector 900 in the closed position with spring-loaded holder block 940 positioned within receptacle 960 such that the pathway into receptacle 960 for a post to enter is obstructed by outer jaw 943 of spring-loaded holder block 940. FIG. 24 shows connector 900 in the open position when spring-loaded holder block 940 is rotated away from receptacle 960 with inner jaw 947 of spring-loaded holder block 940 protruding into receptacle 960 and lever 920 is pressed against housing pin 935.

In another aspect of the embodiment depicted in FIGS. 22-24, the connector 900 is used in a method of provisionally connecting a post to connector 900. More generally, the post used may be part of a manual blade or a retractor frame, for example. In this method, a post, such as post 200, is advanced into receptacle 960. During insertion, the post pushes down inner jaw 947 into an internal cavity of housing 910, causing the remainder of spring-loaded holder block 940 and lever 920 to snap into the closed position with the post secured within receptacle 960. Once lever 920 is in the closed position, lever spring 922 is biased such that lever spring 922 holds lever 920 in the closed position. Additionally, spring-loaded holder block 940 includes flange 949 positioned facing lip 924 of lever 920 such that flange 949 is configured to engage with lip 924 of lever 920 to hold spring-loaded holder block 940 in the closed position.

To remove the post from the closed position within the receptacle, lever 920 is drawn away from receptacle 960, flange 949 and lip 924 disengage and holder spring 942 causes spring-loaded holder block 940 and outer jaw 943 to rotate clockwise from the view shown in FIG. 23 so that inner jaw 947 rotates into receptacle 960 to arrive at the open position. As inner jaw 947 rotates into receptacle 960 and out of the lower portion of the inner cavity of housing 910, the post within the receptacle becomes removable. As mentioned above, holder spring 942 may be biased to the open position such that holder spring 942 holds spring-loaded holder block 940 in the open position once released. In this manner, the post may be removed and connector 900 is once again ready to receive and then provisionally hold a post in receptacle 960 of connector 900. It should be appreciated that, as with post embodiments described elsewhere in the present disclosure, a rotatable top portion of post, such as portion 210, may be rotated to create a fixed engagement when the connector is in the closed position holding the post, and that this is optionally part of any method.

FIGS. 25-27 show post 1200, an alternative embodiment of a post with a non-threaded locking mechanism. As depicted, post 1200 includes base portion 1220 with base rim 1222, outer shaft 1230 with upper rim 1232, internal shaft 1250 attached to the base portion, and cam 1240 rotatably attached to the internal shaft adjacent to the upper rim 1232 via post pin 1212. Base portion 1220 includes a threaded surface to engage a complementary threaded outer surface on a blade or retractor as described elsewhere in the present disclosure. Further, base portion 1220 may include teeth disposed on base rim 1222 configured to form a hirth joint when paired with corresponding teeth disposed on a connector. Internal shaft 1250 may be temporarily attached within base portion 1220, e.g., threadably disposed thereon, or permanently attached, e.g., welded thereon. Upper rim 1232 may be an integral part of outer shaft 1230 or a separate component altogether, e.g., a washer that sits above outer shaft 1230. Outer shaft 1230 may have a lumen 1234 open at both ends of outer shaft 1230 such that internal shaft 1250 may be inserted therethrough. Additionally, as shown in FIG. 27, base portion 1220 may have hollow center 1224 that defines an opening such that outer shaft 1230, internal shaft 1250, and spring 1270 may be inserted therein. Internal shaft may be affixed at the bottom of the hollow center.

In embodiments inclusive of a spring disposed within the post, such as that shown in FIG. 27, spring 1270 may be disposed over inner shaft 1250 and within base portion 1220 such that the spring is positioned at the bottom of base portion 1220 underneath outer shaft 1230. Spring 1270 may be biased in an expanded state without downward force applied to upper rim 1232 of outer shaft 1230. When force is applied to upper rim 1232 of outer shaft 1230 by rotation of cam 1240 such that a wider part of a base of cam 1240 rotates over shaft 1250, outer shaft 1230 extends deeper within hollow center 1224 of base portion 1220 than it would be without force applied through the cam. Through this configuration, spring 1270 controls a separation of upper rim 1232 of outer shaft 1230 and base rim 1222 of base portion 1220. Cam 1240 may include cam handle 1241 which extends from a base of the cam. The base of cam 1240 may be positioned relative to inner shaft 1250 such that upper rim 1232 is disposed between cam 1240 and base rim 1222. It should be appreciated that post 1200 may be used in place of any other post contemplated by the present disclosure.

In a method of connecting a blade or retractor with a post to a connector, the post may be used to adjust a connection from provisional attachment to a fully rigid attachment, as generally described elsewhere in the present disclosure. For post 1200 specifically, steps to adjust the nature of engagement may be as follows. In one embodiment, commencing from the unlocked position, cam handle 1241 is rotated from an orientation generally aligned with a length of post 1200 as shown in FIG. 25, e.g., substantially perpendicular to the longitudinal axis of internal shaft 1250, which causes cam 1240 to push outer shaft 1230 into hollow center 1224 of base portion 1220 as the distance between the upper rim 1232 and post pin 1212 increases and the distance between upper rim 1232 and base rim 1222 decreases (as shown in FIGS. 25 and 26). In some embodiments, when a connector (e.g., connector 100 or connector 900) is provisionally attached to outer shaft 1230 between upper rim 1232 and base rim 1222 of base portion 1220 while post 1200 is in the unlocked position, rotating cam handle 1241 into the locked position will grip the connector between upper rim 1232 and base rim 1222 such that the teeth of the connector interlock with the teeth the base portion and a hirth joint is formed. In this manner, the connector is securely attached to post 1200 in the locked position such that no rotation is permitted between the connector and post 1200. In some circumstances, the base portion may be initially positioned further away from the outer shaft such that there is a larger gap between the connector and the base portion in the open position. In such cases, the base portion may be rotated to reduce such gap either before rotation of the cam arm or after to provide a locking engagement.

To unlock the post, cam handle 1241 is rotated out of the locked position and into the unlocked position. During this step, upper rim 1232 moves closer to post pin 1212 and away from base portion 1220 as spring 1270 reverts to a natural expanded condition. As the distance between upper rim 1232 and base portion 1220 increases, the teeth on the connector may disengage the teeth on base portion 1220 such that the post and connector may be released from the engagement. In this manner, the connector returns to a provisional connection with post 1200 as cam 1240 no longer securely holds the teeth of the connector into the teeth of base portion 1220.

It is to be understood that the disclosure set forth herein includes any possible combinations of the particular features set forth above, whether specifically disclosed herein or not. For example, where a particular feature is disclosed in the context of a particular aspect, arrangement, configuration, or arrangement, that feature may also be used, to the extent possible, in combination with and/or in the context of other particular aspects, arrangements, configurations, and arrangements of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative arrangements and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A connector attachable to a free end of a support arm comprising:

a housing extending from a proximal end to a distal end, the housing including a receptacle adjacent to the distal end;

a holder block movably disposed in the housing, the holder block adjustable between a retracted position where a tip of the holder block is outside of the receptacle and a holding position where the tip is at least partially within the receptacle; and a bumper block movably disposed in the housing, a surface of the bumper block defining part of the receptacle, the bumper block being biased in an expanded position such that the holder block is held in the retracted position by the bumper block and movement of the bumper block from the expanded position to a compressed position releases the holder block the holding position, wherein the connector is adapted to receive a post disposed on a retraction device, the post being loadable into the receptacle to cause the bumper block to move away from the holder block to the compressed position such that the holder block is repositioned to holds the post within the receptacle while the post remains rotatable relative to the connector.

2. The connector of claim 1, wherein the holder block is manually adjustable from the holding position to the retracted position.

3. The connector of claim 1, wherein the holder block is pivotably movable or slidably movable.

4. The connector of claim 1, further comprising a spring disposed between the bumper block and the housing, wherein the spring has an angled orientation with respect to a longitudinal axis of the holder block.

5. The connector of claim 1, wherein a loading axis passes through a center of the receptacle, a center of a side-facing periphery of the receptacle and the bumper block, the holder block being entirely offset from the loading axis when the holder block is in the retracted position.

6. A system comprising:
   the connector of claim 1; and
   a hand-held blade with a post disposed thereon, the post being loadable into the receptacle of the connector, and the post including a rotatable head adapted to fix the hand-held blade to the connector.

7. The system of claim 6, wherein the connector includes a first set of teeth and the hand-held blade includes a second set of teeth, the first and second sets of teeth engageable with each other when the head of the post is rotated, thereby fixing the hand-held blade to the connector.

8. A system for engagement of a retractor arm to a support arm comprising:
   a connector attached at an end of a support arm, the connector comprising:
   a housing extending from a proximal end to a distal end, the housing including a receptacle adjacent to the distal end;
   a holder block movably disposed in the housing, the holder block adjustable between a retracted position where a tip of the holder block is outside of the receptacle and a holding position where the tip is at least partially within the receptacle; and
   a bumper block slidable into a compressed position and away from the holder block; and
   a retraction device engageable with the connector, the retraction device including a post disposed thereon, the post comprising:
   a head; and
   a shaft extending from the head, the shaft adapted to be received in the receptacle,
   wherein, when the shaft is loaded into the receptacle of the housing, the connector limits movement of the retraction device along a longitudinal axis of the shaft, and
   wherein, when the shaft is loaded into the receptacle of the housing and the head of the post is rotated such that the head applies force to a surface of the connector, the retraction device is rotatably fixed relative to the connector.

9. The system of claim 8, wherein the post further comprises a threaded base disposed in an opening of the retraction device, the threaded base having a bore defined by an inner threaded surface such that a threaded surface of the shaft is rotatably disposed in the bore.

10. The system of claim 9, wherein the threaded base includes the second set of teeth being disposed thereon.

11. The system of claim 8, wherein when the post is advanced into and received in the receptacle, the holder block passively moves from the retracted position to the holding position.

12. The system of claim 8, wherein at least one of a top surface and a bottom surface of the housing includes a first set of teeth disposed adjacent to the receptacle and at least one of the post and the retraction device includes a second set of teeth such that when the shaft is loaded into the receptacle, the first set of teeth engage the second set of teeth.

13. The system of claim 8, wherein the retraction device is a hand-held blade or a portion of a retractor frame.

14. The system of claim 8, wherein the bumper block is adjustable from an expanded position to the compressed position, and the bumper block being adapted to hold the holder block in the retracted position when the bumper block is in the expanded position and to release the holder block when moved into the compressed position.

15. The system of claim 8, wherein the holder block is pivotably movable or slidably movable.

16. A method of securing a retractor frame or a hand-held blade to a support arm comprising:
   loading a post of the retractor frame or hand-held blade into a receptacle on a connector of the support arm to move a bumper block away from a holder block to allow the holder block to move into part of the receptacle such that the post is held within the receptacle of the connector while being freely rotatable with respect to the connector; and
   rotating a head of the post in a first direction until a first gripping surface of the connector engages a second gripping surface of the post, thereby rotationally fixing the post to the connector.

17. The method of claim 16, wherein rotating the head further comprises engaging a first set of teeth on the connector with a second set of teeth on the retractor frame or the hand-held blade.

18. The method of claim 17, wherein rotating the head further comprises engaging a third set of teeth on the head of the post with a fourth set of teeth on the connector.

19. The method of claim 16, wherein the bumper block defines a part of the receptacle of the connector when the post is loaded into the receptacle, and wherein the movement of the bumper block causing the holder block to be released from an initial retracted position to a holding position partially enveloping the post within the receptacle.

20. The method of claim 19, further comprising removing the post from the receptacle, the removing step comprising:
   rotating the head of the post in a second direction opposite the first direction;
   pulling on and holding the holder block to move the holder block from the holding position to the retracted position, wherein the holder block is held in the retracted position by the bumper block; and
   withdrawing the post from the receptacle of the connector.

21. A system for engagement of a retractor arm to a support arm comprising:
   a connector attached at an end of a support arm, the connector comprising:
   a housing extending from a proximal end to a distal end, the housing including a receptacle adjacent to the distal end; and
   a holder block movably disposed in the housing, the holder block adjustable between a retracted position where a tip of the holder block is outside of the receptacle and a holding position where the tip is at least partially within the receptacle; and
   a retraction device engageable with the connector, the retraction device including a post disposed thereon, the post comprising:
   a head; and
   a shaft extending from the head, the shaft adapted to be received in the receptacle,
   wherein, when the shaft is loaded into the receptacle of the housing, the connector limits movement of the retraction device in a longitudinal axis of the shaft,
   wherein, when the shaft is loaded into the receptacle of the housing and the head of the post is rotated such that the head applies force to a surface of the connector, the retraction device is rotatably fixed relative to the connector, and wherein the post further comprises a threaded base disposed in an opening of the retraction device, the threaded base having a bore defined by an inner threaded surface such that a threaded surface of the shaft is rotatably disposed in the bore.

22. A method of securing a retractor frame or a hand-held blade to a support arm comprising:

loading a post of the retractor frame or hand-held blade into a receptacle on a connector of the support arm to move a holder block into part of the receptacle such that the post is held in the connector while being freely rotatable in the connector; and rotating a head of the post in a first direction until a first gripping surface of the connector engages a second gripping surface of the post, thereby rotationally fixing the post to the connector, wherein rotating the head includes engaging a first set of teeth on the connector with a second set of teeth on the retractor frame or the hand-held blade and engaging a third set of teeth on the head of the post with a fourth set of teeth on the connector.

* * * * *